United States Patent [19]

Yabe et al.

[11] Patent Number: 5,702,347
[45] Date of Patent: Dec. 30, 1997

[54] ENDOSCOPE SYSTEM INCLUDING ENDOSCOPE AND DISPOSABLE PROTECTION COVER

[75] Inventors: Hisao Yabe, Hachioji; Yoshihiro Iida, Tama; Akira Suzuki; Hideo Ito, both of Hachioji; Yoshio Tashiro, Hino; Minoru Yamazaki; Osamu Tamada, both of Hachioji; Masaaki Nakazawa, Hino; Koji Yamaya, Hachioji, all of Japan

[73] Assignee: Olympus Optical Co., Ltd., Tokyo, Japan

[21] Appl. No.: 631,133

[22] Filed: Apr. 12, 1996

Related U.S. Application Data

[62] Division of Ser. No. 36,890, Mar. 25, 1993.

[30] Foreign Application Priority Data

| Jan. 27, 1993 | [JP] | Japan | 5-001786 |
| Jan. 28, 1993 | [JP] | Japan | 5-001901 |
| Jan. 28, 1993 | [JP] | Japan | 5-001902 |
| Jan. 29, 1993 | [JP] | Japan | 5-002051 |

[51] Int. Cl.⁶ .................................................. A61B 1/04
[52] U.S. Cl. .................................... 600/121; 600/123
[58] Field of Search ................................ 600/121, 122, 600/123, 124, 125

[56] References Cited

U.S. PATENT DOCUMENTS

| 3,035,691 | 5/1962 | Rasmussen et al. |
| 3,633,758 | 1/1972 | Morse. |
| 4,108,211 | 8/1978 | Tanaka. |
| 4,216,767 | 8/1980 | Aoshiro. |
| 4,288,882 | 9/1981 | Takeuchi. |
| 4,366,901 | 1/1983 | Short. |
| 4,404,963 | 9/1983 | Kohri. |
| 4,646,722 | 3/1987 | Silverstein et al. |
| 4,715,360 | 12/1987 | Akui et al. ........................ 128/4 |
| 4,721,097 | 1/1988 | D'Amelio. |
| 4,741,326 | 5/1988 | Sidall et al. |
| 4,779,727 | 10/1988 | Taterka et al. |
| 4,825,850 | 5/1989 | Opie et al. |
| 4,858,001 | 8/1989 | Milbank et al. ................... 128/6 X |
| 4,869,238 | 9/1989 | Opie et al. |
| 4,877,033 | 10/1989 | Seitz. |
| 4,878,485 | 11/1989 | Adair. |
| 4,907,396 | 3/1990 | Opie et al. |
| 4,947,827 | 8/1990 | Opie et al. ........................ 128/4 |
| 4,991,564 | 2/1991 | Takahashi et al. |
| 4,991,565 | 2/1991 | Takahashi et al. |
| 5,025,778 | 6/1991 | Silverstein et al. |
| 5,042,112 | 8/1991 | Dunklee. |
| 5,050,585 | 9/1991 | Takahashi. |
| 5,105,942 | 4/1992 | van Veen et al. |
| 5,131,537 | 7/1992 | Gonzales. |
| 5,198,894 | 3/1993 | Hicks. |
| 5,201,908 | 4/1993 | Jones. |

(List continued on next page.)

FOREIGN PATENT DOCUMENTS

| 0341719A1 | 11/1989 | European Pat. Off. |
| 0349479A1 | 1/1990 | European Pat. Off. |
| 2805298A1 | 8/1978 | Germany. |
| 376128B2 | 10/1989 | Japan. |
| 3264037A | 11/1991 | Japan. |
| 4325138 | 11/1992 | Japan ............................ 128/4 |

*Primary Examiner*—Beverly M. Flanagan
*Attorney, Agent, or Firm*—Watson Cole Stevens Davis, P.L.L.C.

[57] ABSTRACT

In an endoscope system including an endoscope having an insertion section and an operation section and a disposable protection cover having an insertion section cover having formed therein a forceps channel and a forceps inlet opening through which a forceps can be inserted into the forceps channel, said forceps inlet opening is selectively closed by a forceps plug which is made of resilient material and separately formed from the insertion section cover. The forceps plug is preferably formed such that it can be detachably secured to a forceps inlet opening of an ordinary coverless (without-cover) endoscope.

6 Claims, 39 Drawing Sheets

U.S. PATENT DOCUMENTS

| | | |
|---|---|---|
| 5,217,001 | 6/1993 | Nakao et al. . |
| 5,237,984 | 8/1993 | Williams, III et al. . |
| 5,257,617 | 11/1993 | Takahashi . |
| 5,301,657 | 4/1994 | Lafferty et al. . |
| 5,334,142 | 8/1994 | Paradis . |
| 5,359,991 | 11/1994 | Takahashi et al. .......................... 128/4 |
| 5,363,843 | 11/1994 | Daneshvar . |
| 5,419,311 | 5/1995 | Yabe et al. . |

FIG_1

FIG_3
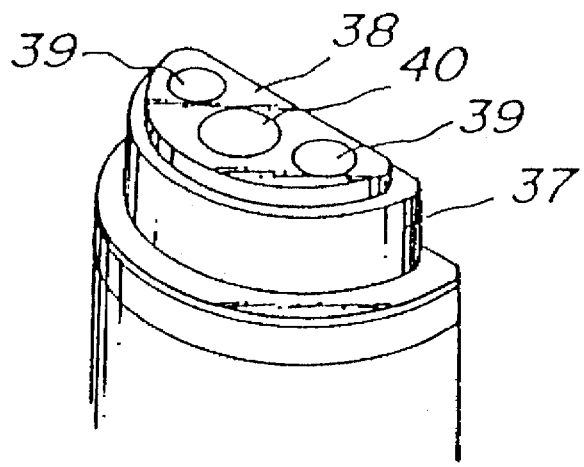
FIG_4
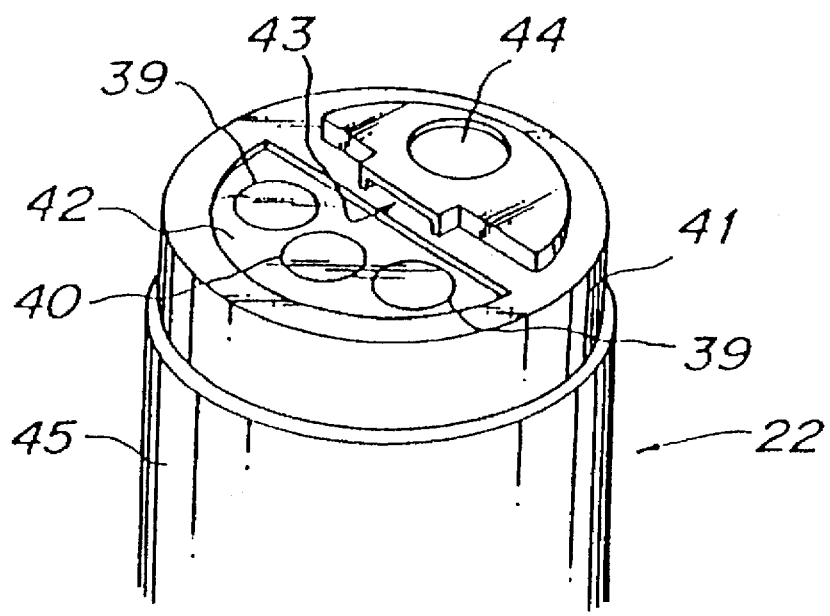

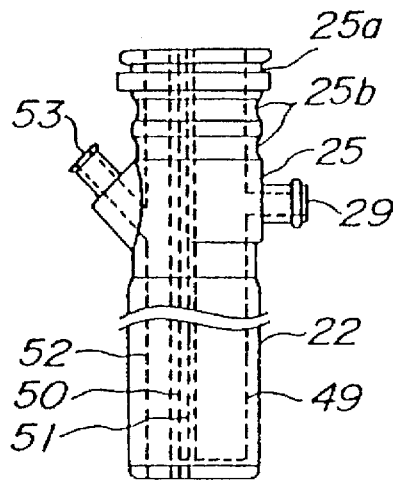
FIG_6A
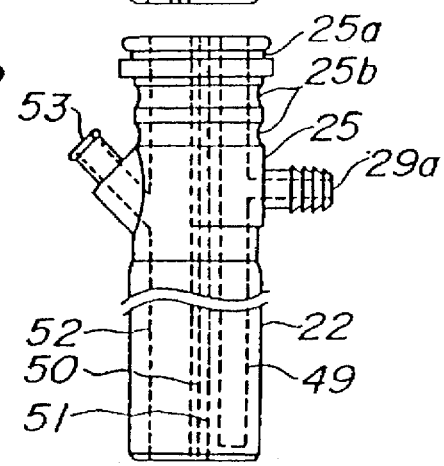
FIG_6B
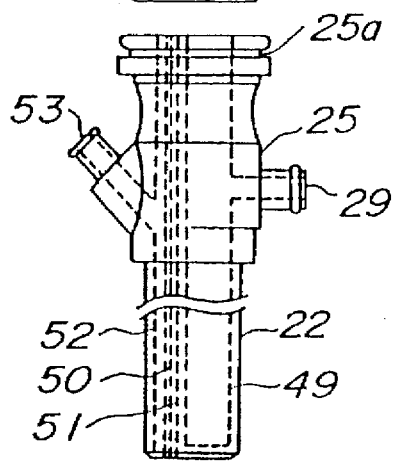
FIG_6C
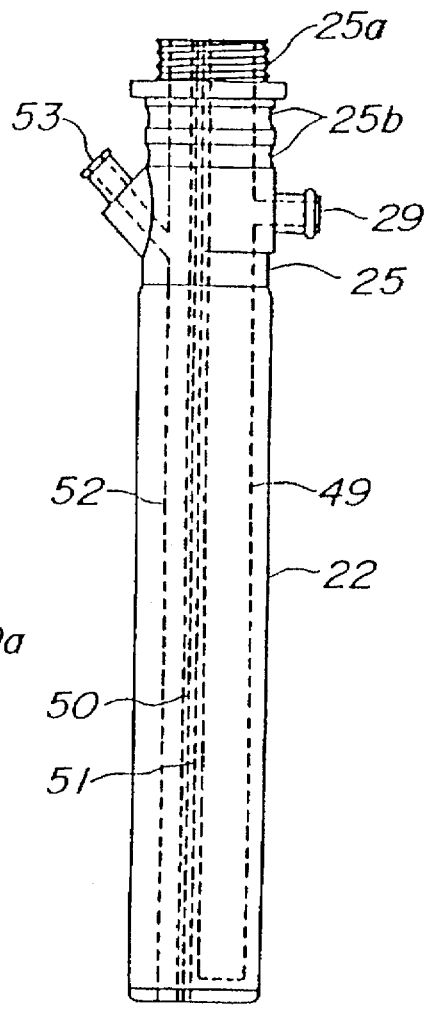
FIG_6D

FIG_7
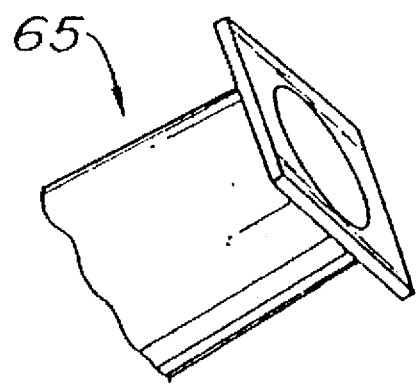

FIG_9

FIG_10

FIG_11

FIG_12

FIG_13

FIG._14

FIG_17
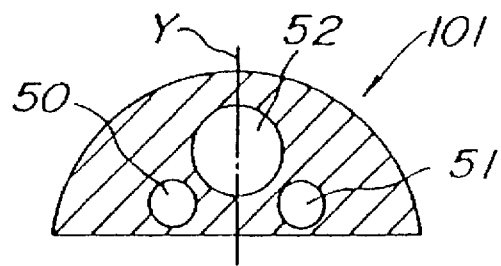
FIG_18
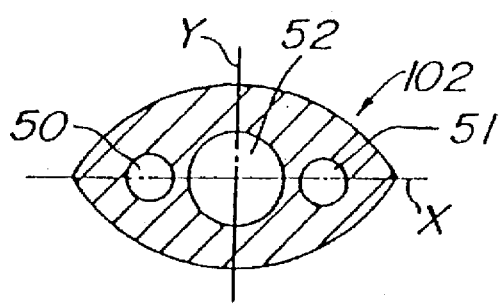
FIG_19
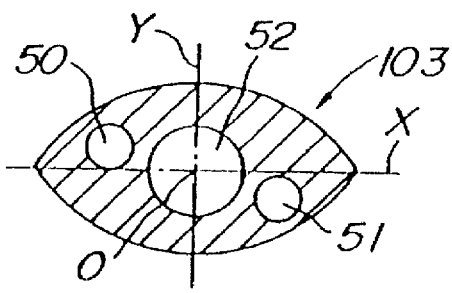

FIG_20
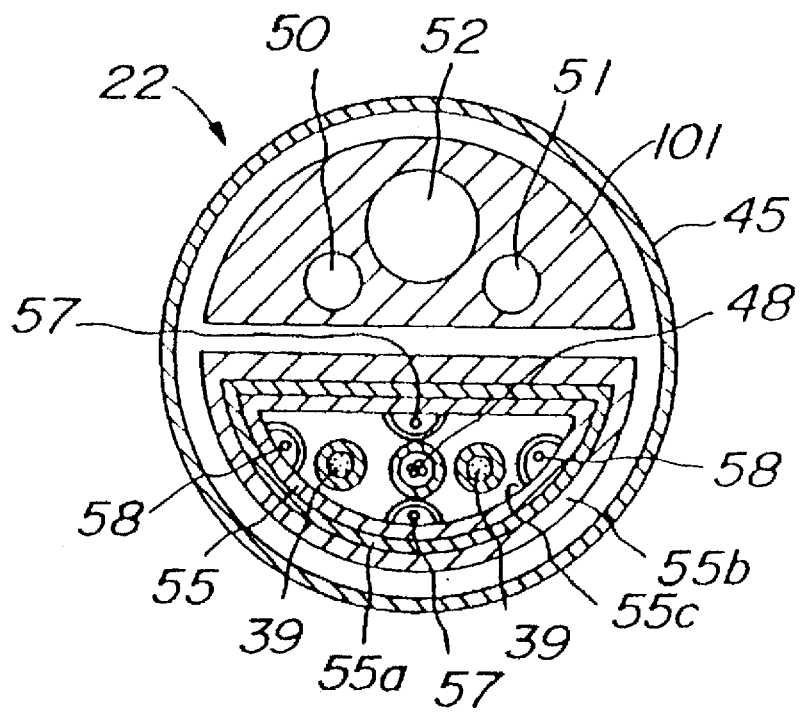
FIG_21
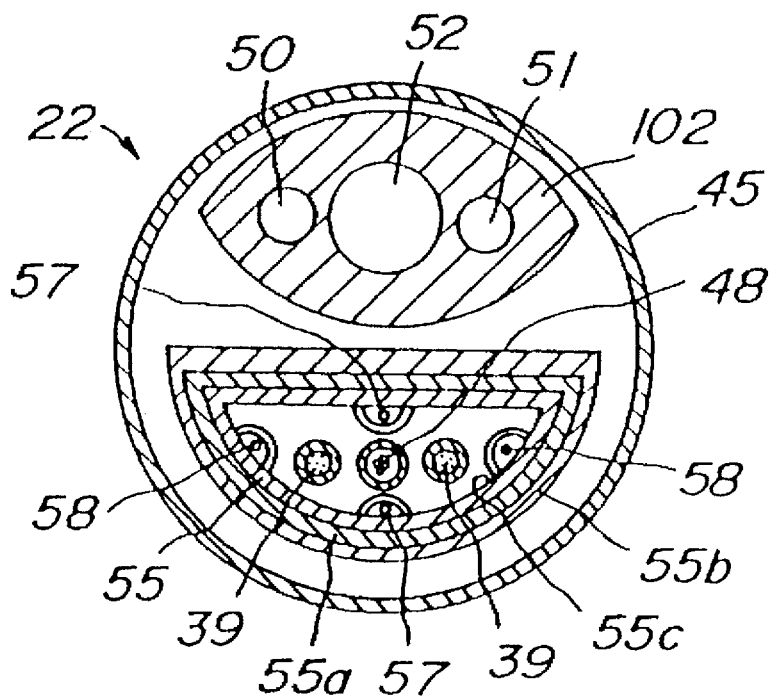

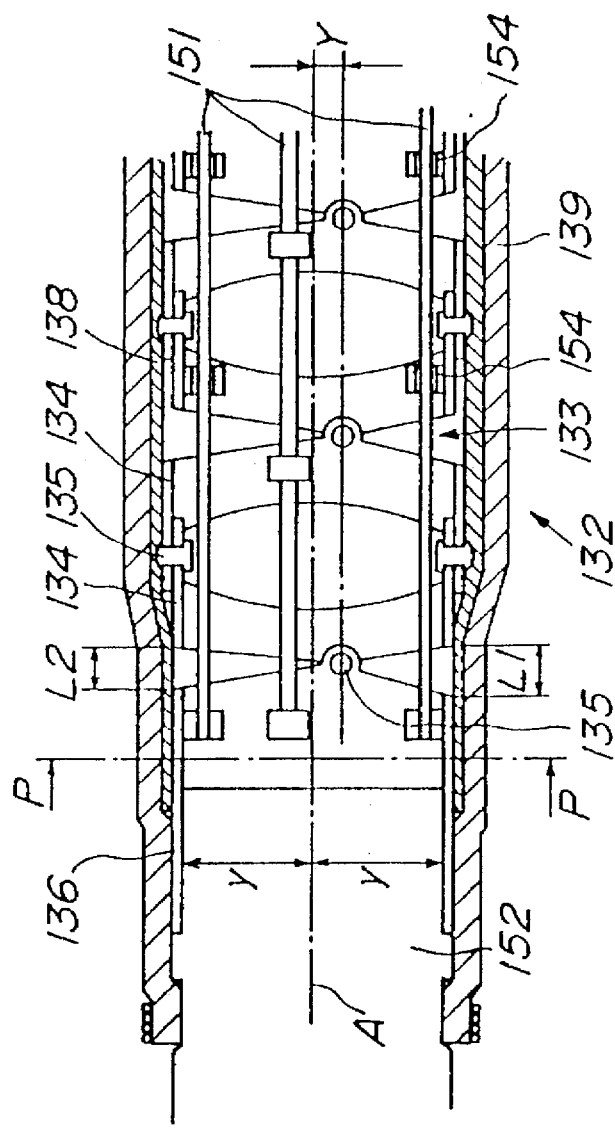
FIG._25A
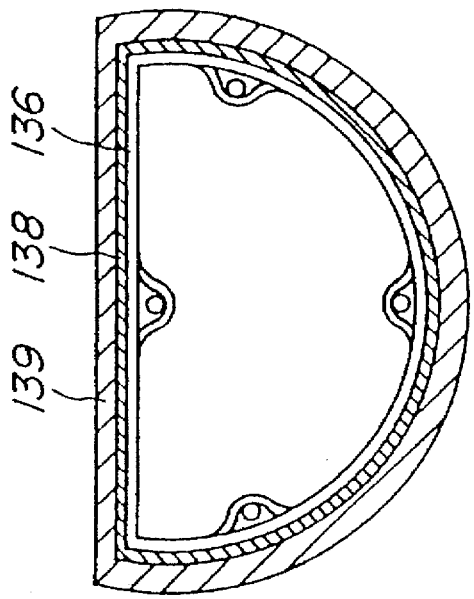
FIG._25B

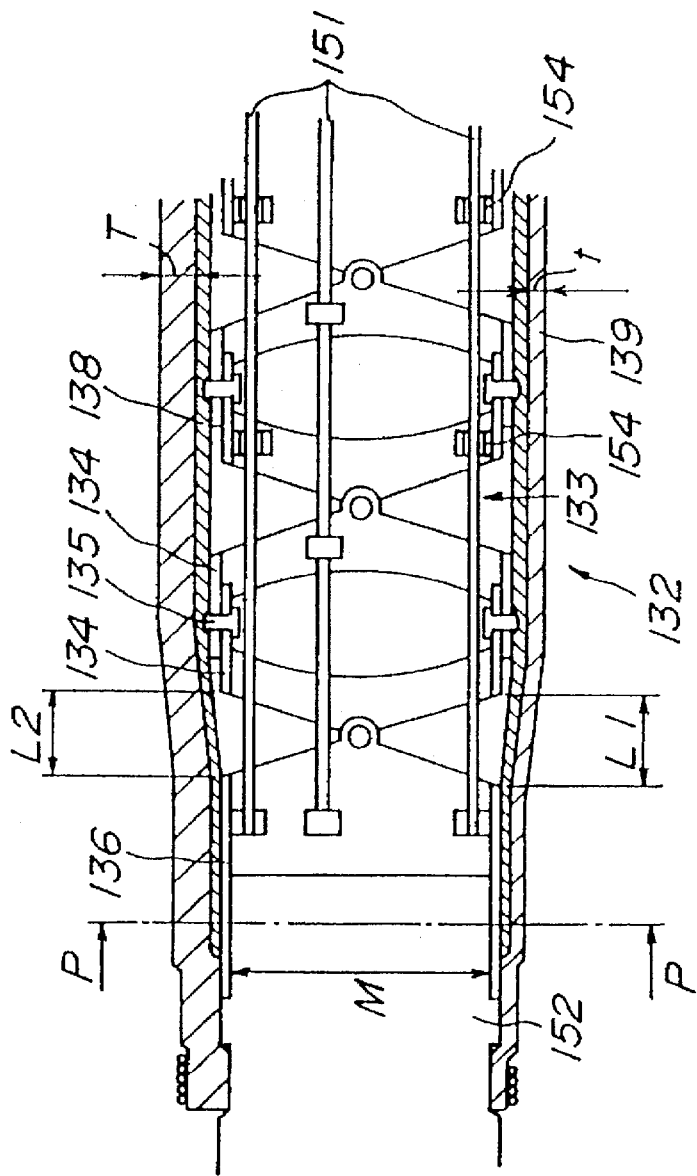
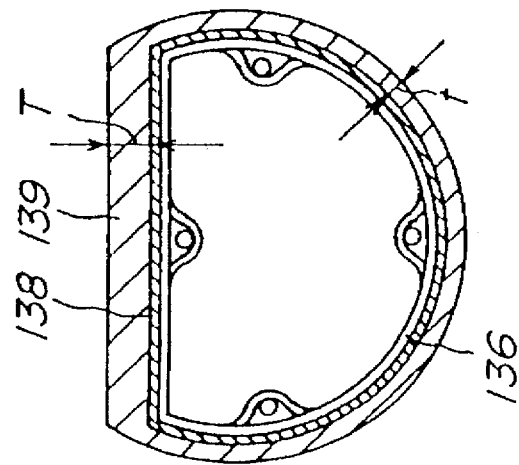
FIG. 26A
FIG. 26B

FIG_27
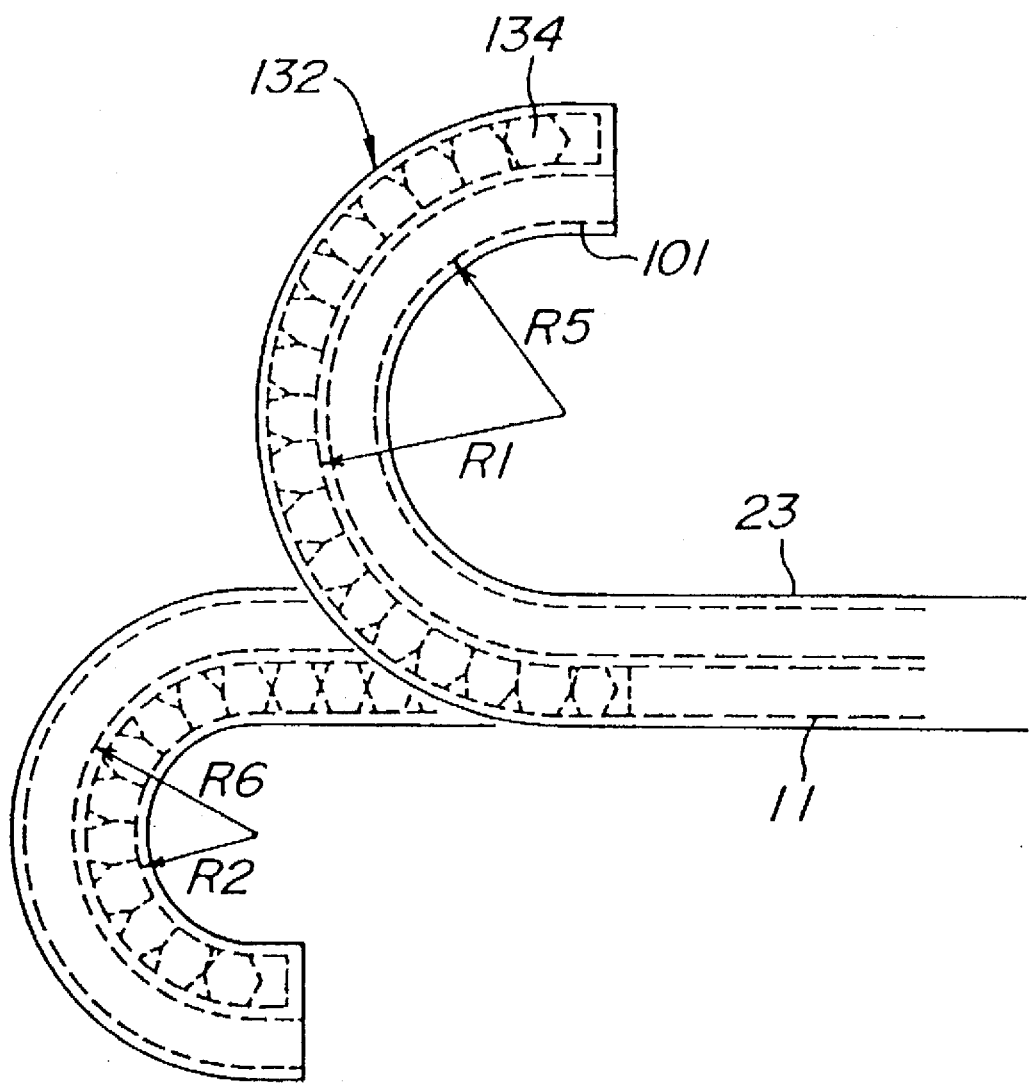

FIG_30A
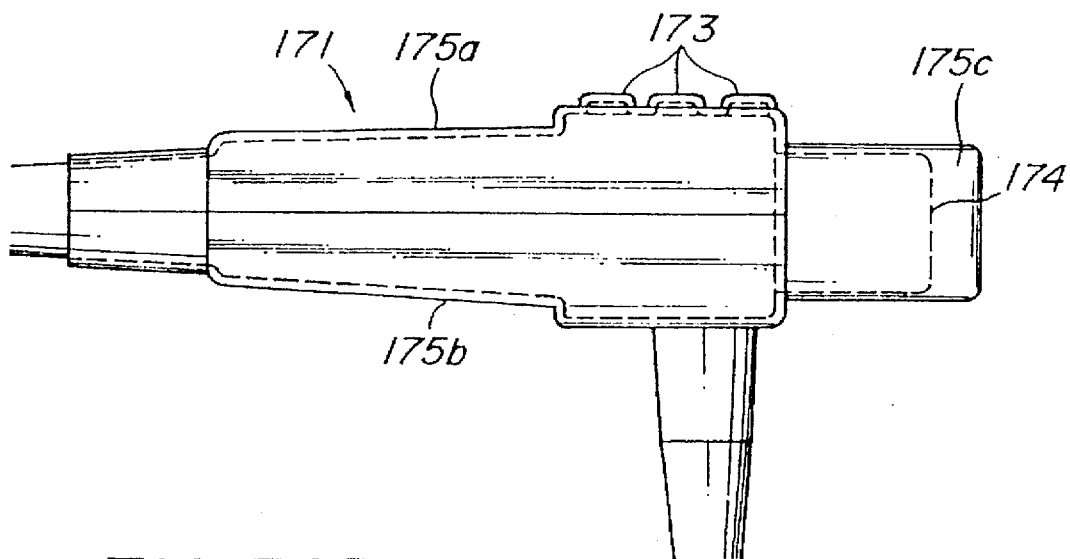
FIG_30B
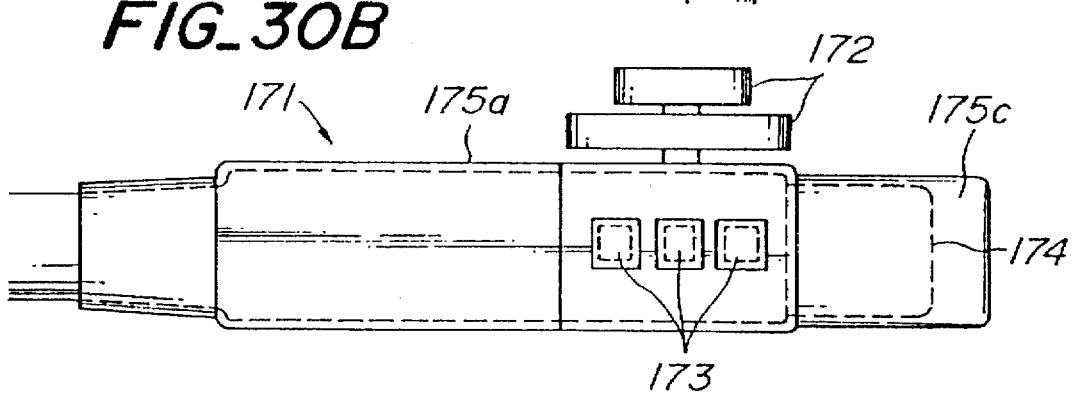

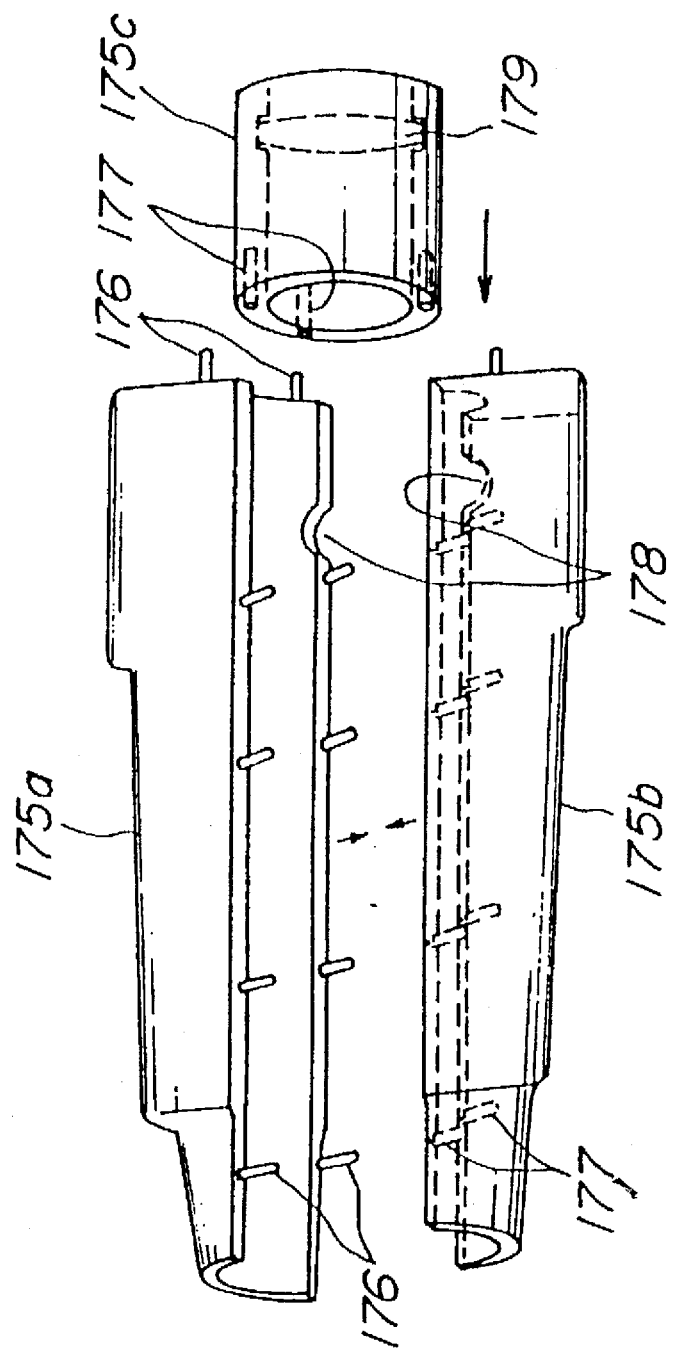
FIG._31

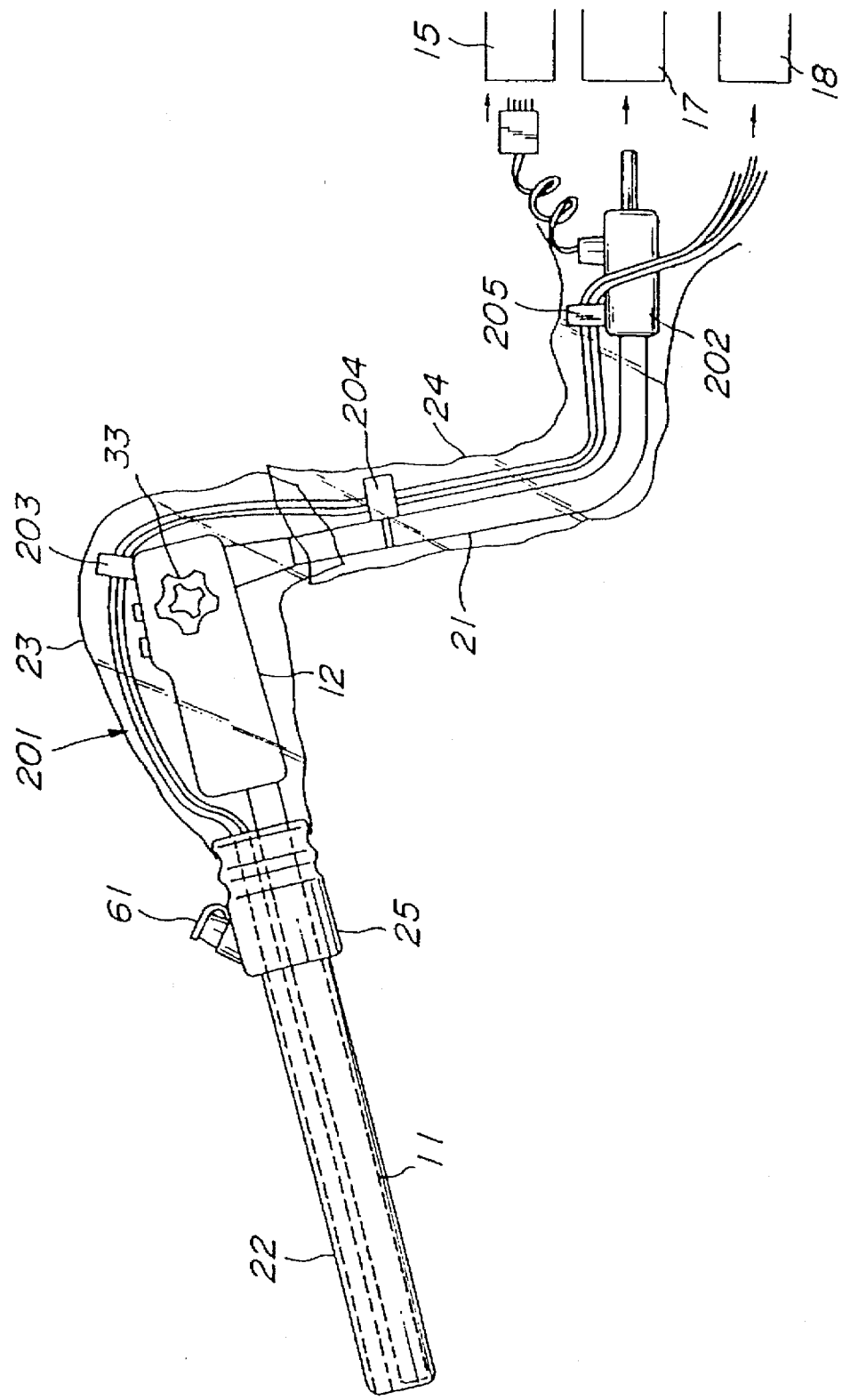

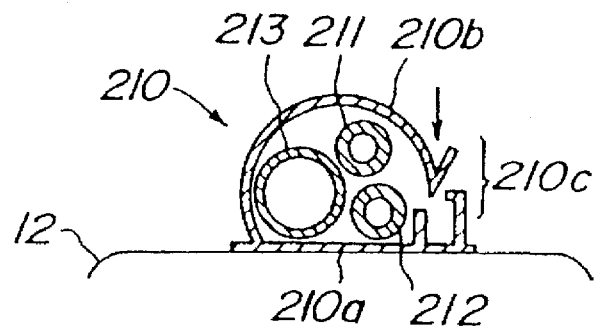
FIG_33
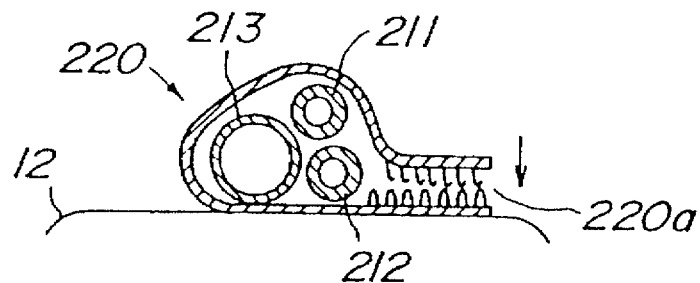
FIG_34
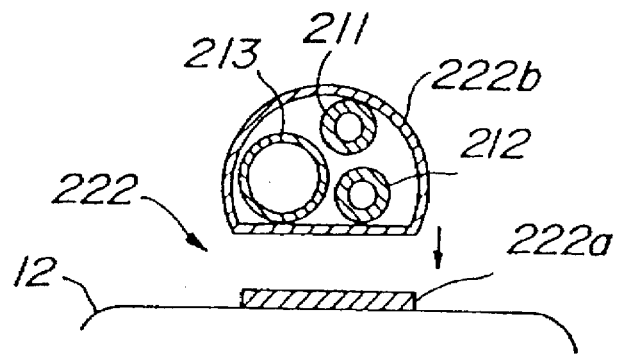
FIG_35
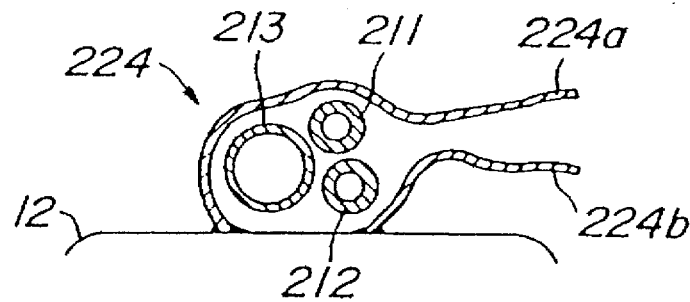
FIG_36

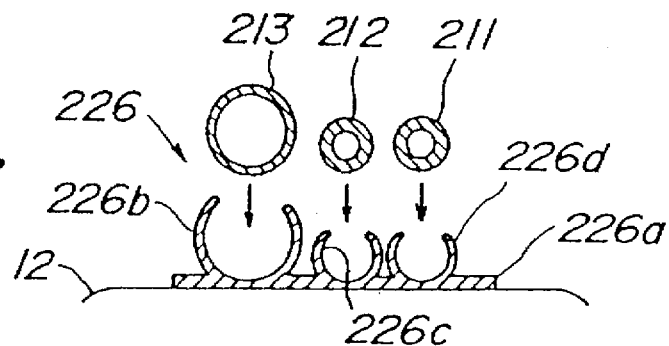
FIG._37
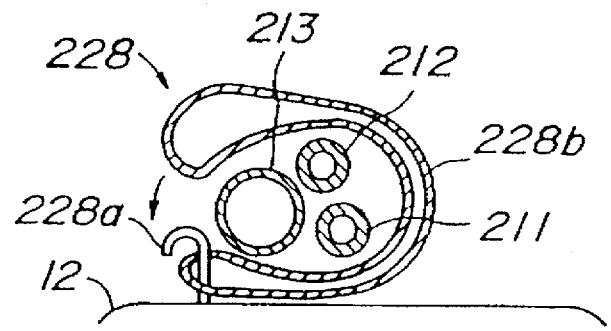
FIG._38
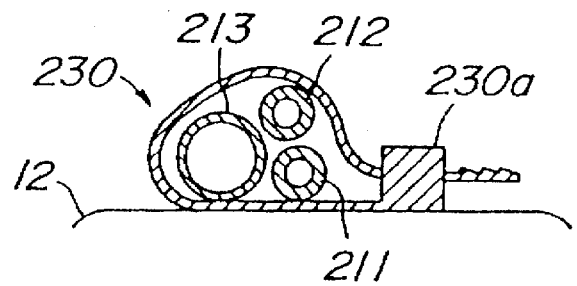
FIG._39
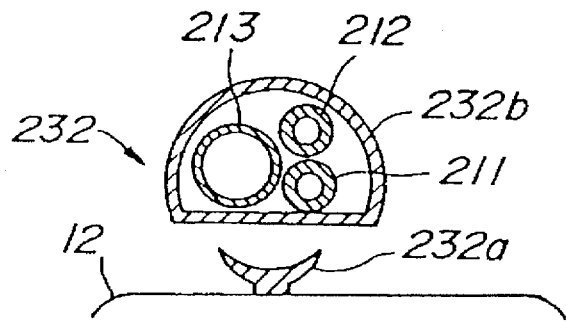
FIG._40

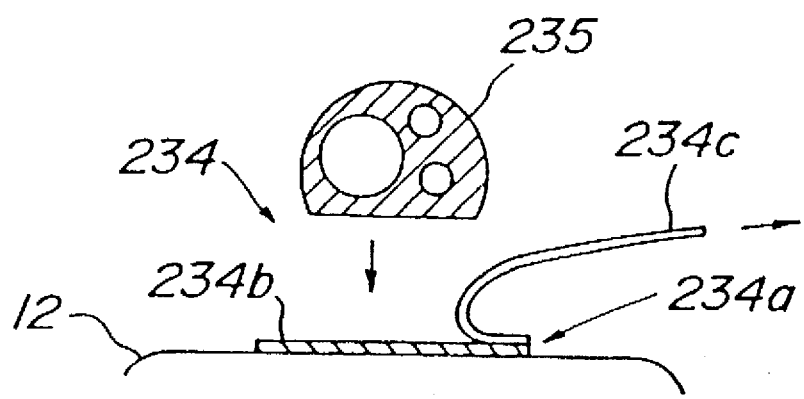
FIG_41

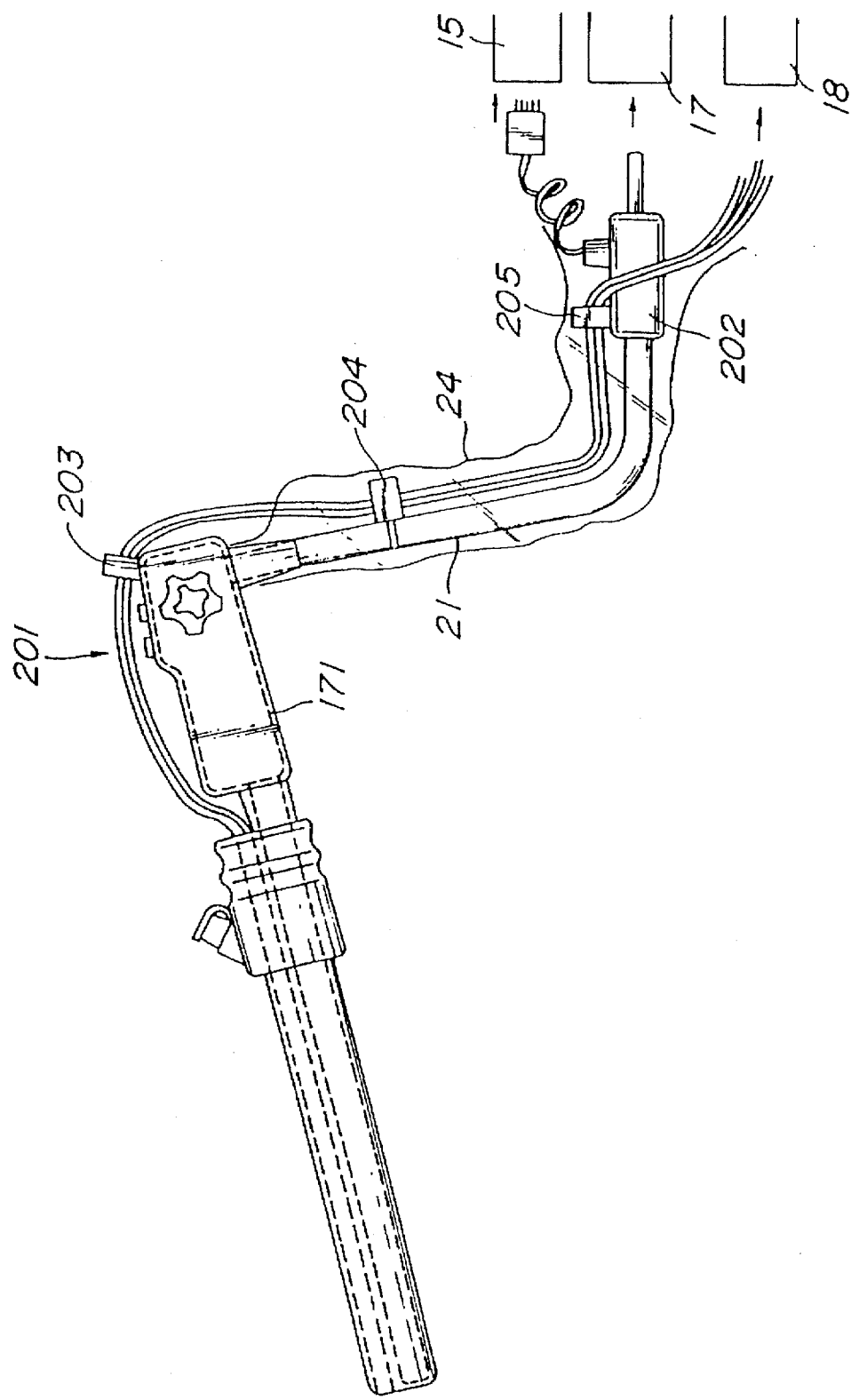

FIG_43
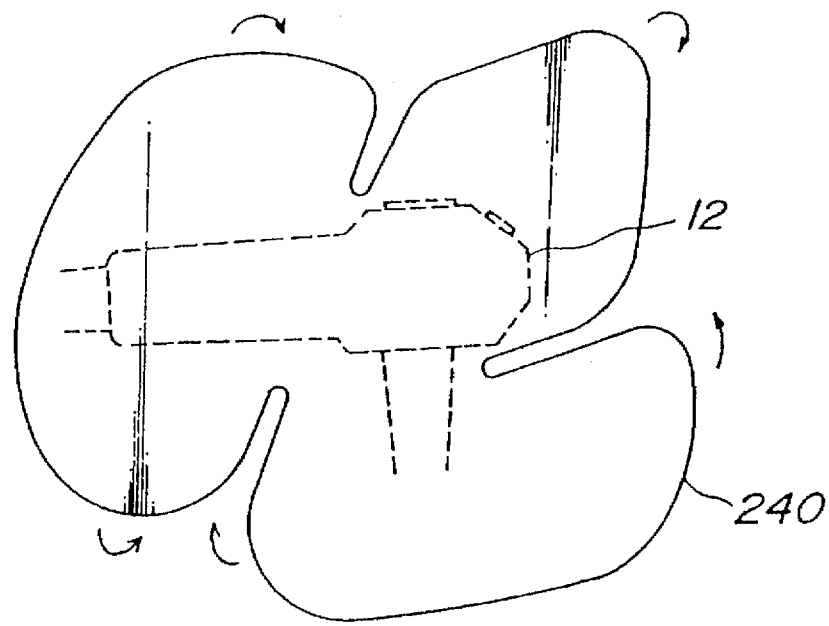
FIG_44
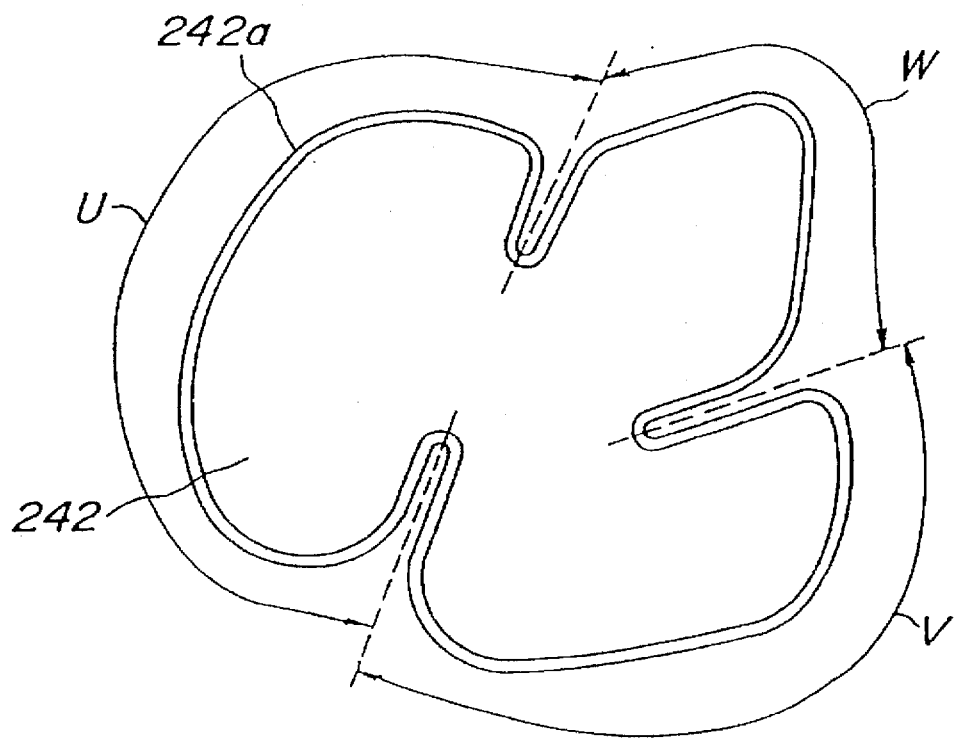

FIG_45
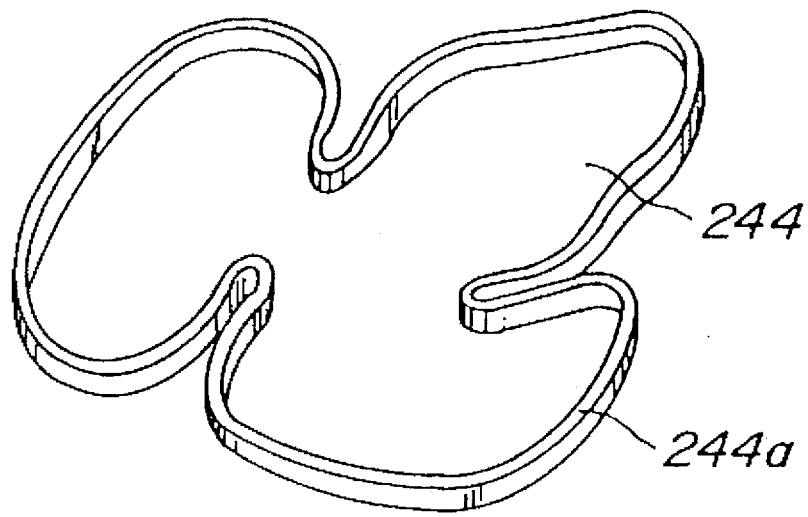
FIG_46
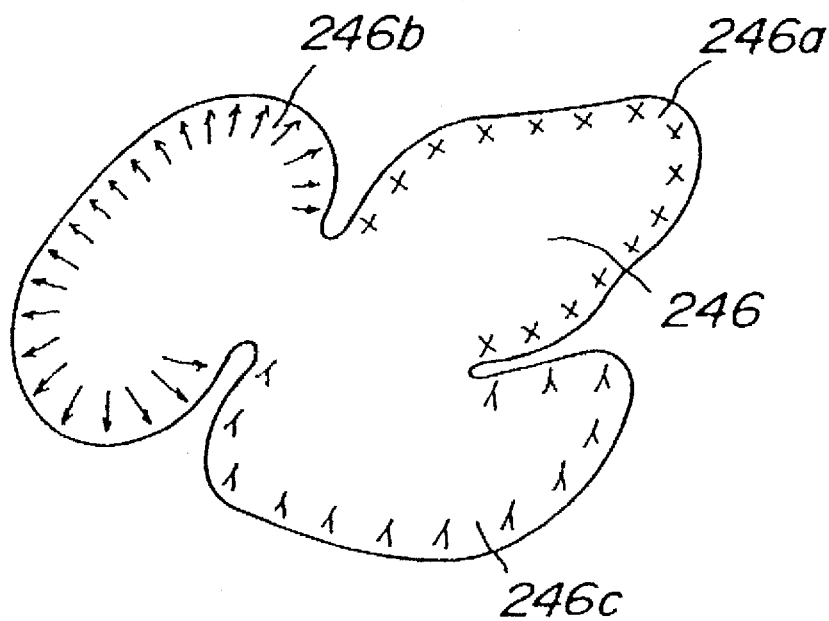

FIG_47
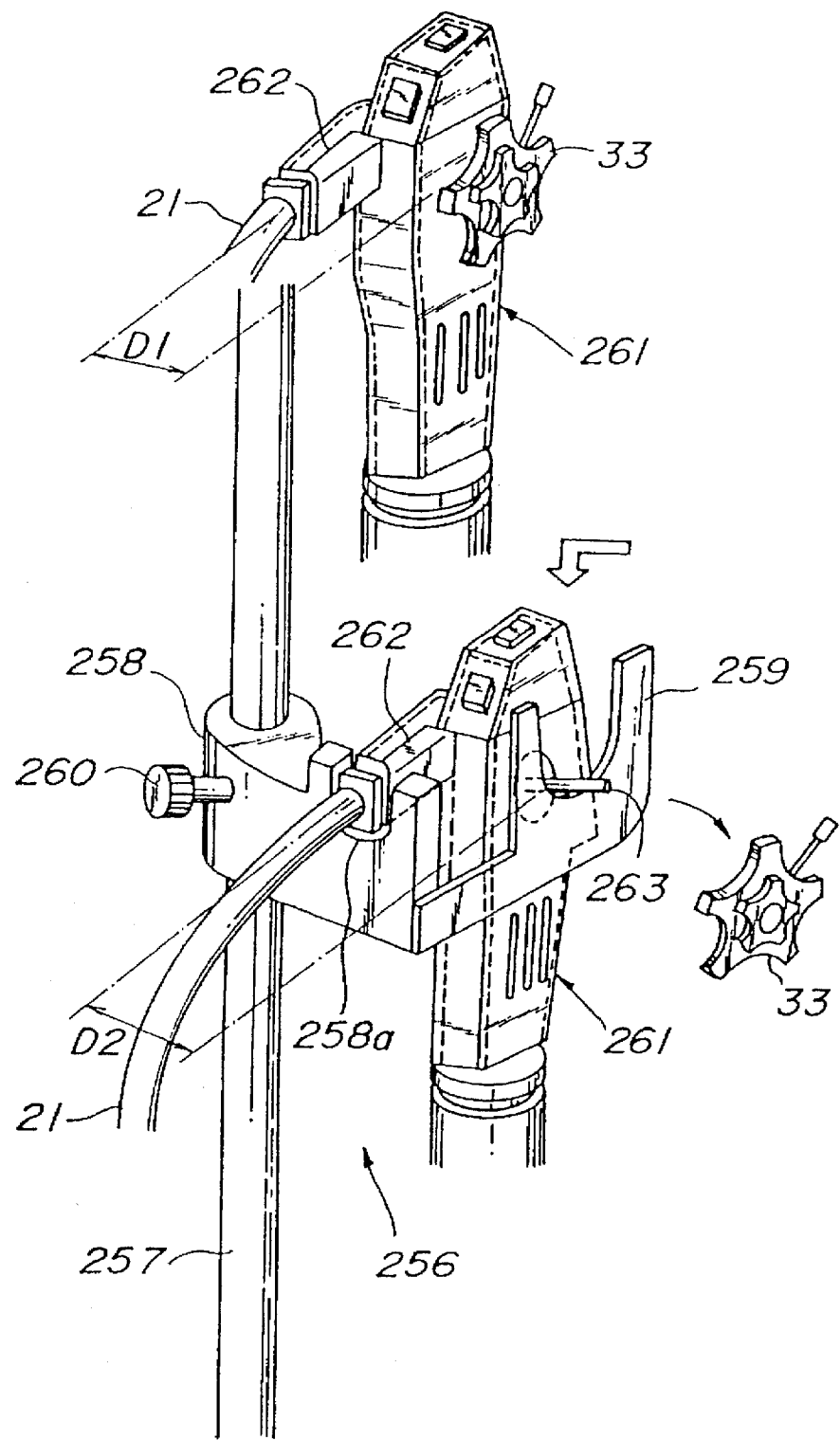

FIG_49
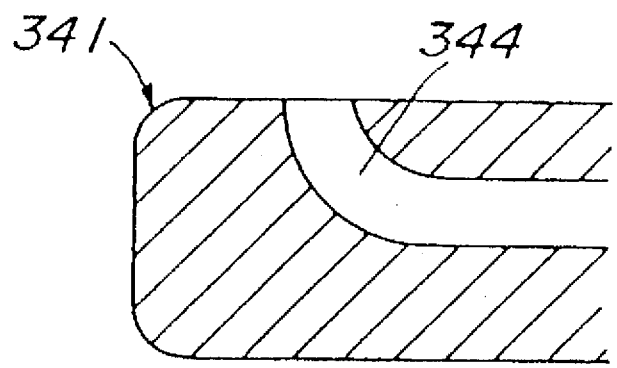
FIG_50
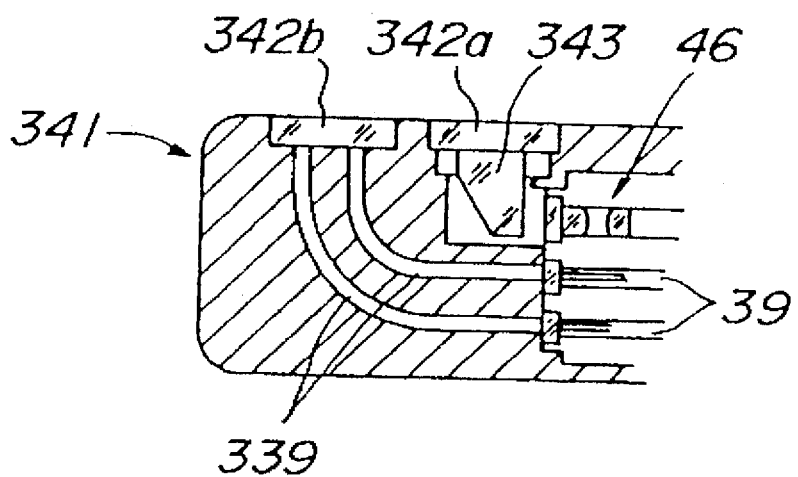

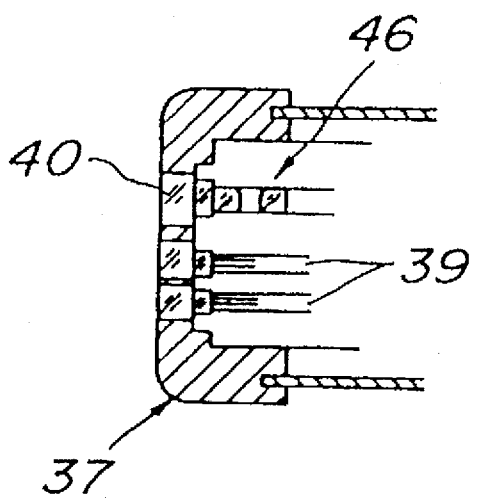
FIG_52

FIG_53
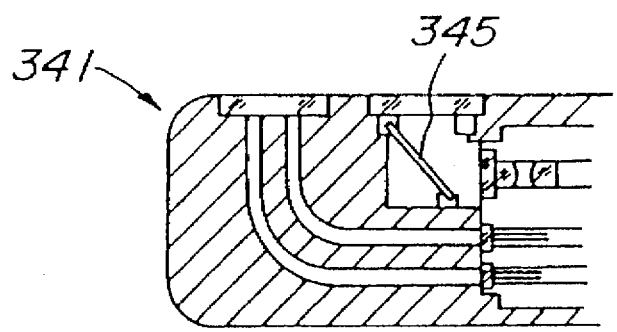
FIG_54
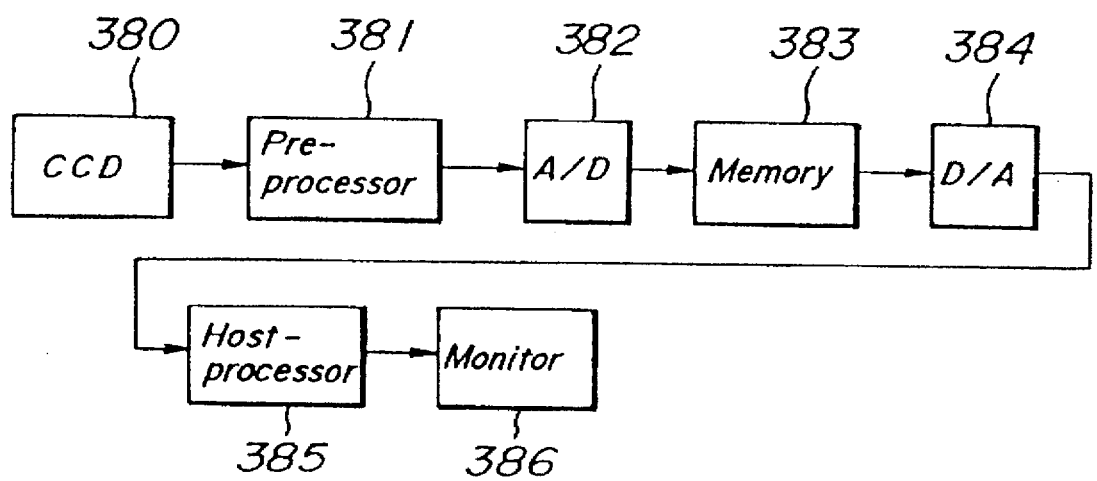

FIG_55
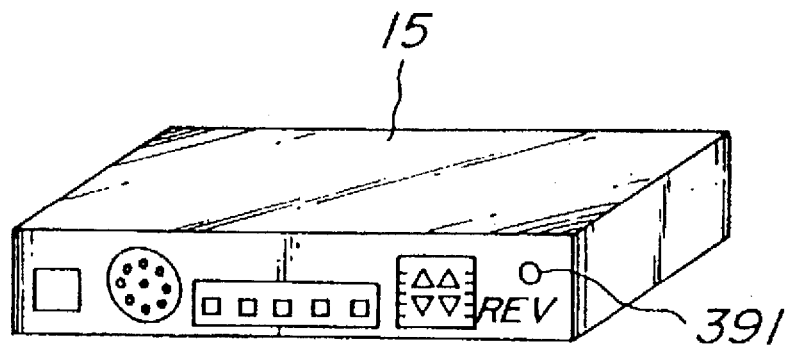
FIG_56
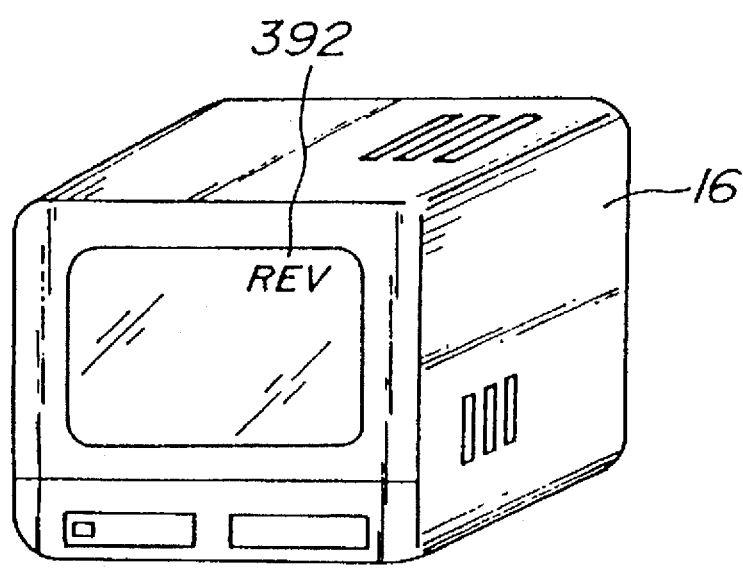

ENDOSCOPE SYSTEM INCLUDING ENDOSCOPE AND DISPOSABLE PROTECTION COVER

This is a division of application Ser. No. 08/036,890 filed Mar. 25, 1993, pending.

BACKGROUND OF THE INVENTION

1. Field of the Invention

The present invention relates to an endoscope system including an endoscope and a disposable protection cover for covering the endoscope, and also relates to a disposable protection cover and an endoscope for use in such an endoscope system.

2. Description of the Related Art

An endoscope system has been widely utilized for providing diagnostic and therapeutic indications for coeliac cavities of patients and for internal inspection of mechanical structures. To this end, various kinds of endoscopes have been developed. For instance, in order to inspect or treat the oesophagus, stomach and duodenum, upper endoscopes have been utilized. Further, colonoscopes have been developed to examine colons and sigmoidoscopes have been proposed to inspect rectums and sigmoid colons. When the endoscope is used an insertion portion of the endoscope has to be inserted into a cavity of a patient, so that the outer surface of the insertion section of the endoscope is contaminated with living tissues and liquids. Such a contaminated endoscope can not be successively used for other patients. Therefore, once the endoscope is used to diagnose and/or treat a patient, it is necessary to clean and sterilize the endoscope. Of course, the cleaning of the endoscope requires substantial time and during this cleaning time, it is impossible to perform the endoscopic procedures by using this endoscope. In order to mitigate such an idle time, it is necessary to prepare a large number of endoscopes. However, endoscopes are rather expensive, so that it is practically difficult to prepare a large number of endoscopes particularly in a small hospital or clinic. Therefore, in almost all hospitals and clinics, in practice, after the endoscope has been used for examining or treating a patient, the endoscope is immediately cleaned. Typically, this cleaning requires several minutes to ten minutes. In order to effect the complete washing and sterilize on, the cleaning has be to performed for several tens of minutes.

Further, the endoscope has various channels such as an air channel, a water channel, a suction channel, and a forceps channel which extend along the insertion section from a proximal end to a distal end thereof, and these channels, except the forceps channel are connected via tubes to respective devices such as an air supply pump, a water supply pump, water suction pump and an air suction pump. These channels are subjected to contact with living tissues and liquids. However, in order to clean these channels of the endoscope completely, a relatively long time is required. Thus, the endoscope can not be utilized efficiently for the long cleaning time. In a large hospital or clinics, a large number of endoscopes may be prepared in order to mitigate the problem of cleaning time. However, this solution results in an increase in the operation cost. Further, in small clinics, it is practically impossible to prepare a number of expensive endoscopes.

Moreover, the endoscope might be broken during cleaning and the usable life of the endoscope is liable to is shortened by the cleaning.

In order to avoid the above explained various problems, there has been proposed an endoscope system, in which the endoscope is covered with a disposable protection sheath-like cover having channels formed therein. For instance, U.S. Pat. Nos. 4,721,097, 4,741,326, 4,825,850, 4869,238, 4,991,564, 4,991,565, 5,050,585 disclose various kinds of disposable protection sheath-like covers having channels formed therein. In U.S. Pat. No. 4,646,722, there is shown an endoscope system in which the endoscope is covered with a protection sheath, while a tube having channels formed therein is inserted into a U-shaped cutout formed in an outer surface of the endoscope along a longitudinal axis thereof. Upon diagnosis, the insertion section of the endoscope is covered with the protection sheath, and after the inspection, the sheath is removed from the insertion section and is then discarded. Therefore, it is no longer necessary to clean the endoscope after every inspection.

In the above mentioned U.S. Patent Specifications, the protection sheath-like cover is constructed to cover only the insertion section of the endoscope, but does not cover an operation section of the endoscope. It should be noted that the operation section of the endoscope is handled by doctors and operators, and thus is brought into contact with the living tissues and liquids of a patient. Therefore, in order to remove the contamination of the operation section of the endoscope due to such living tissues and liquids, it is advantageous to cover not only the insertion section, but also the operation section of the endoscope. In European Patent Publication No. 0 349 479 A1, there is disclosed an endoscope system, in which not only the insertion section, but also the operation section of the endoscope are covered with a disposable protection cover. That is to say, the protection cover comprises a sheath-like portion for covering the insertion section of the endoscope and a bag-like portion for covering the operation section, the sheath-like portion and bag-like portion being integrally formed. It has been also proposed to form the sheath-like portion and bag-like portion as separate covers. For instance, in European Patent Publication No. 0 341 719 A1, there is proposed another known endoscope system, in which an insertion section of an endoscope is covered with a disposable protection sheath-like cover and an operation section of the endoscope is covered with a disposable protection bag-like cover which is mated or joined with the protection sheath-like cover in order to prevent contamination through the junction of the sheath-like cover and the bag-like cover.

In order to treat a cavity of a patient body, it has been proposed to arrange a forceps channel within the sheath-like cover into which an endoscope is inserted. In this case, it is desired to close an inlet opening of the forceps channel through which forceps are inserted. However, in the known disposable protection cover, nothing has been proposed regarding the construction of the forceps plus for closing the above mentioned inlet opening of the forceps channel. The forceps plug may be integrally formed with the protection cover or may be provided separately from the protection cover.

When the forceps plug is provided integrally with the disposable protection cover, even if the forceps plug is deteriorated, damaged or broken during the examination, the forceps plug can not be exchanged by a new one. When the forceps plug is damaged, a liquid passing through the forceps channel might flow from the forceps plug. In order to exchange the damaged forceps plug, it is necessary to remove the endoscope and protection cover from the patient, remove the insertion section of the endoscope from the insertion section cover, and then insert the insertion section into a new protection cover having a new forceps plug. This results in that the examination time is prolonged and the patient is subjected to the undesired operations of removing and inserting the insertion section of the endoscope covered with the protection cover. If the deteriorated forceps plug is used, the liquid containing stains and bloods might be ejected from the forceps plug when the forceps channel is used as the suction channel, so that the operators and the floor of examination room are contaminated.

As explained above, in the disposable protection cover there are formed a forceps channel, an air supply conduit channel and on water supply conduit channel. These channels are extended within the protection cover. In a lateral cross section of the protection cover, these channels are arranged in a substantially semicircular space and the endoscope is inserted into the remaining substantially semicircular space. It should be noted that the distal end of the insertion section of the endoscope is bent in right and left directions and/or up and down directions by operating one or two angle knobs provided on the operation section of the endoscope. In the known endoscope the distal end portion of the insertion section is bent in a symmetrical manner with respect to a neutral position. For instance, the distal end of the insertion section can be bent upward and downward by the same angles. When such an insertion section of the endoscope is inserted into the protection cover, the bend angles of the distal end in the upward and downward directions become different from each other. That is to say, if the above mentioned channels are arranged in an upward portion within the protection cover, the upward bend angle becomes smaller than the downward bending angle. Such asymmetry in the bending angle makes the operation of the endoscope difficult. For instance, when the distal end of the endoscope is bent downward, the tip portion of the protection cover might be brought into contact with a cavity wall of the patient to damage the cavity wall.

Further, the conduit channels such as the forceps channel, the air supply channel and the water supply channel formed in the disposable protection cover communicate with an external apparatus including a light source, an air pump, a water pump, a suction pump and a signal processing device. Usually the conduit channels are formed by flexible tubes and those tubes communicate with the above mentioned devices. The tubes are extended from the operation section cover to the external apparatus. In this case, in order not to prevent a smooth movement of the operation section of the endoscope, these tubes can not be extended tightly. Therefore, the tubes are liable to be hung loosely and this might cause inconvenience in the operation, particularly when the operation section is covered with the operation section cover and the universal cord is covered with a universal cord cover.

Further, when the tubes are loosely hung, there is a fear that they might be brought into contact with the floor. This causes a serious contamination of the sterilized protection cover. In order to avoid such drawbacks, it is considered to bind these tubes and an assembly of tubes with a sterilized protection tube cover. However, in this case, the assembly of tubes with the protection tube cover is loosely hung and the tubes are moved within the protection tube cover when the operation section is moved during the examination.

SUMMARY OF THE INVENTION

The present invention has for its object to provide a novel and useful disposable protection cover for use in an endoscope system including an endoscope having an insertion section to be inserted into a cavity under inspection and an operation section to which a proximal end of the insertion section is connected and a disposable protection cover for covering at least the insertion section of the endoscope and having a forceps channel and a forceps inlet opening communicated with the forceps channel, in which the forceps inlet opening can be selectively closed by means of a forceps plug which is formed separately from the protection cover, so that when the forceps plug is damaged, it can be easily replaced by a new one during examination.

It is another object of the invention to provide a novel and useful endoscope system including an endoscope system including an ordinary without-cover (coverless) endoscope which is used without a disposable protection cover and has an insertion section to be inserted into a cavity under inspection, an operation section to which proximal end of the insertion section is connected, a forceps channel extending within said insertion section is and a forceps inlet opening communicated with the forceps channel, a special with-cover endoscope which is used with a disposable protection cover and has an insertion section to be inserted into a cavity under inspection, an operation section to which a proximal end of the insertion section is connected, a forceps channel extending within the insertion section and a forceps inlet opening communicated with the forceps channel and a disposable protection cover having an insertion section cover for covering the insertion section of the with-cover endoscope, a forceps channel extending within the insertion section cover and a forceps inlet opening communicated with the forceps channel, in which the forceps inlet openings of the ordinary without-cover endoscope and protection cover can be selectively closed commonly by a forceps plug which is formed separately from the protection cover and the without-cover endoscope.

It is another object of the invention to provide a novel and useful endoscope system including an endoscope having an insertion section to be inserted into a cavity under inspection and an operation section to which a proximal end of the insertion section is connected, and a disposable protection cover having an insertion section cover for covering the insertion section of the endoscope and conduit channels extending within said insertion section cover, in which the distal end of the insertion section can be bent symmetrically without being affected by the conduit channels.

It is another object of the invention to provide a novel and useful endoscope system including an endoscope having an insertion section to be inserted into a cavity under inspection and an operation section to which a proximal end of the insertion section is connected, and a disposable protection cover having an insertion section cover for covering the insertion section of the endoscope and conduit channels extending within the insertion section cover, in which said conduit channels can be effectively prevented from being contaminated.

According to a first aspect of the invention, a disposable protection cover for use in an endoscope system including an endoscope having an insertion section to be inserted into a cavity under inspection and an operation section to which a proximal end of the insertion section is connected and a disposable protection cover for covering at least the insertion section of the endoscope, comprises:

an insertion section cover for covering the insertion section of the endoscope;
a forceps channel formed within the insertion section cover to extend from a proximal end to a distal end of the insertion section cover;
a forceps inlet opening formed at a proximal end of the insertion section cover to be communicated with said forceps channel; and a forceps plug formed separately from the insertion section cover and endoscope for being detachably secured to the forceps inlet opening.

In the disposable protection cover according to the invention, the forceps plug is formed independently from the protection cover, so that even if the forceps plug is damaged during the examination, the damaged forceps plug can be easily exchanged by a new one without removing the insertion section from the cavity under inspection as well as from the protection cover. Therefore, there is no fear that liquid will flow from the forceps inlet opening and contamination can be effectively avoided.

According to a second aspect of the invention, an endoscope system comprises:

an ordinary without-cover (coverless) endoscope being used without a disposable protection cover and having an insertion section to be inserted into a cavity under inspection, an operation section to which a proximal end of the insertion section is connected, forceps channel extending within the insertion section and a forceps inlet opening communicated with the forceps channel;

a special with-cover (covered) endoscope being used with a disposable protection cover and having an insertion section to be inserted into a cavity under inspection, an operation section to which a proximal end of the insertion section is connected, forceps channel extending within the insertion section and a forceps inlet opening communicated with the forceps channel; a disposable protection cover having an insertion section cover for covering the insertion section of the with-cover endoscope, a forceps channel extending within the insertion section cover and a forceps inlet opening communicated with the forceps channel; and a forceps plug which is formed separately from the protection cover and without-cover endoscope and is detachably secured to the forceps inlet openings of the ordinary without-cover endoscope and protection cover commonly.

In the above mentioned endoscope system according to the invention, the forceps plug can be commonly used for the protection cover and without-cover endoscope, so that it is no longer necessary to select a suitable forceps plug and the operation becomes easy.

According to the third aspect of the present invention, in an endoscope system including an endoscope having an insertion section to be inserted into a cavity under inspection and an operation section to which a proximal end of the insertion section is connected, and a disposable protection cover having an insertion section cover for covering the insertion section of the endoscope and conduit channels extending within the insertion section cover, the improvement being characterized in that the endoscope comprises means for making a radius of curvature of a bending movement of the distal end of the insertion section in a first direction, which is opposite to a second direction in which the conduit channels are arranged viewed in a radial direction, smaller than a radius of curvature of the bending movement of the distal end of the insertion section in the second direction.

In such an endoscope system according to the invention, upon examination, the insertion section of the endoscope is inserted into the insertion section cover of the disposable protection cover and then the distal end of the insertion section of the endoscope is bent by operating the angles knobs provided on the operation section of the endoscope, the distal end can be bent symmetrically in the first and second directions without being affected by the conduit tubes, so that the operation of the endoscope is improved.

According to a fourth aspect of the present invention, in an endoscope system including an endoscope having an insertion section to be inserted into a cavity under inspection and an operation section to which a proximal end of the insertion section is connected, and a disposable protection cover having an insertion section cover for covering the insertion section of the endoscope and conduit channels extending within said insertion section cover, the improvement being characterized in a means for fixing conduit tubes communicated with the conduit channel tubes to at least one of the operation section of the endoscope, universal cord, connector and operation section cover.

In such an endoscope system, the conduit channel tubes are fixed to at least one of the operation section of the endoscope, universal cord, connector of the universal cord and operation section cover of the disposable protection cover, and therefore the conduit channel tubes are no longer hung loosely and can be effectively prevented from being brought into contact with the floor to avoid the contamination.

BRIEF DESCRIPTION OF THE DRAWINGS

FIG. 3 is a perspective view depicting the distal end of the insertion section of the endoscope;

FIG. 4 is a perspective view illustrating the construction of the distal end of the insertion section cover;

FIGS. 6A, 6B, 6C and 6D are side views depicting several embodiments of the insertion section cover according to the invention;

FIG. 7 is a perspective view representing another embodiment of the forceps inlet opening;

FIG. 17 is a cross sectional view showing an embodiment of the multilumen tube;

FIG. 18 is a cross sectional view depicting another embodiment of the multilumen tube;

FIG. 19 is a cross sectional view illustrating still another embodiment of the multilumen tube;

FIG. 20 is a cross sectional view depicting an embodiment of the insertion section cover having the multilumen tube shown in FIG. 17;

FIG. 21 is a cross sectional view showing another embodiment of the insertion section cover having the multilumen tube of FIG. 18;

FIGS. 25A and 25B are cross sectional views illustrating another embodiment of the bending portion of the insertion section according to the invention;

FIGS. 26B and 26B are cross sectional views depicting another embodiment of the bending portion;

FIG. 27 is a schematic view showing the bending movement of the assembly of the endoscope and protection cover;

FIGS. 30A and 30B are views showing another embodiment of the operation section cover according to the invention;

FIG. 31 is an exploded view of the operation section cover shown in FIGS. 30A and 30B;

FIG. 32 is a side view illustrating an embodiment of the endoscope system according to the invention;

FIGS. 33, 34, 35, 36, 37, 38, 39, 40 and 41 are cross sectional views depicting several embodiments of the conduit tube fixing member according to the invention;

FIG. 42 is a side view showing another embodiment of the endoscope system according to the invention FIG. 43, 44, 45 and 46 are cross sectional views illustrating several embodiments of the insertion section cover according to the invention;

FIG. 47 is a perspective view depicting an embodiment of the operation section supporting device according to the invention;

FIGS. 49 and 50 are cross sectional views cut along lines A—A and B—B, respectively in FIG. 48;

FIG. 52 is a cross sectional view cut along a line C—C in FIG. 51;

FIG. 53 is a cross sectional view depicting another embodiment of the insertion section cover according to the invention;

FIG. 54 is a block diagram illustrating an embodiment of the video processor according to the invention;

FIG. 55 is a perspective view showing an embodiment of the video processor; and

FIG. 56 is a perspective view depicting an embodiment of the monitor.

EXPLANATION OF THE PREFERRED EMBODIMENTS

Figure 1:
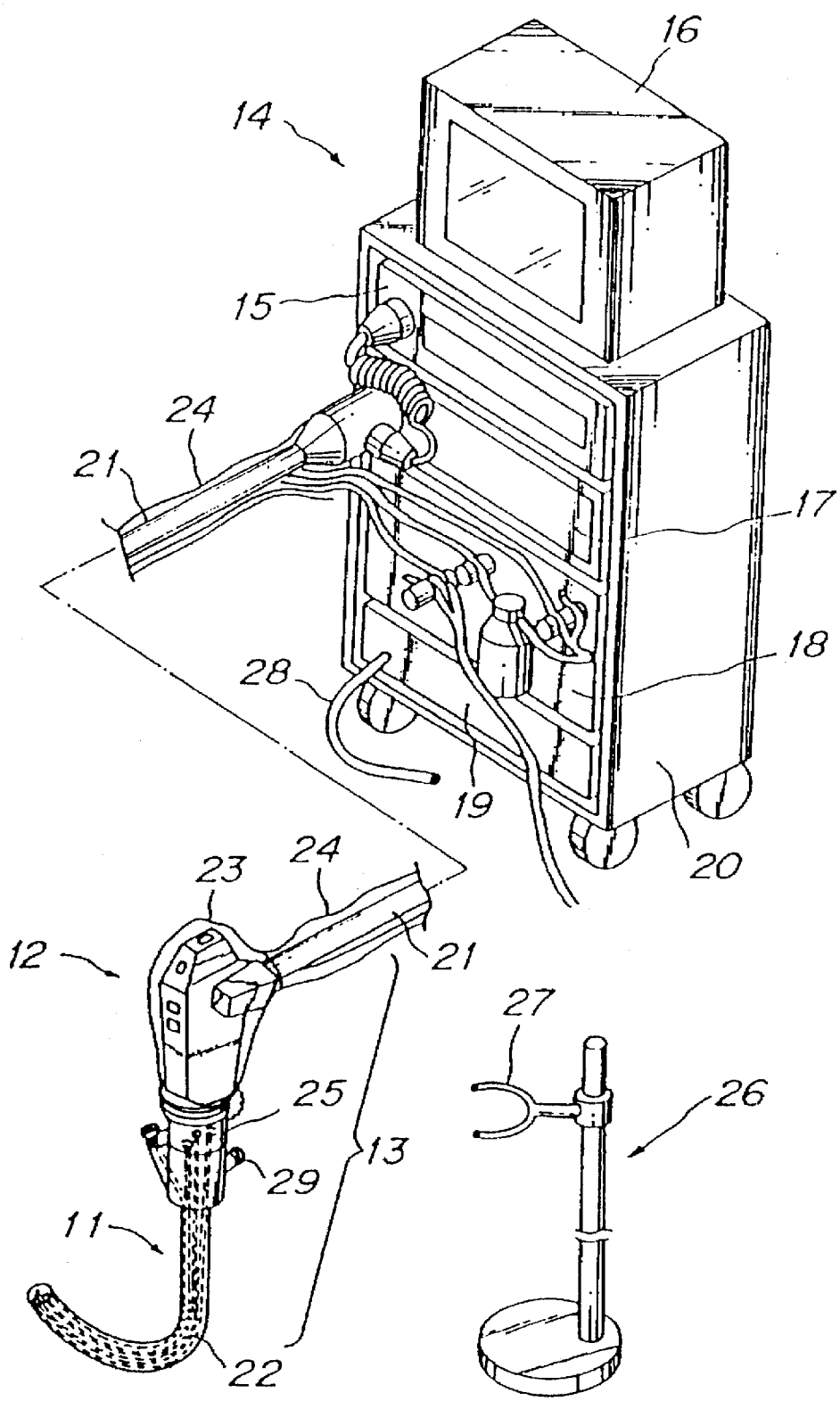
FIG. 1 is a perspective view showing the whole construction of an embodiment of the endoscope system according to the invention.

FIG. 1 is a schematic view showing an embodiment of the endoscope system according to the invention including an endoscope apparatus and disposable protection cover. The endoscope apparatus comprises an endoscope 13 having an insertion section 11 and an operation section 12 with which a proximal end of the insertion section is coupled, and an external apparatus 14 coupled with the endoscope 13. The external apparatus 14 comprises a video processor 15 having a circuit for driving a solid state image sensor provided within a distal end of the insertion section 11 and a circuit for processing an image signal read out of the solid state image sensor, a monitor device 16 for displaying an image of an object under inspection by processing the image signal supplied from the video processor 15, a light source device 17 for emitting light for illuminating an inside of a cavity by means of a light guide optical fiber bundle extending within the insertion section 11, a fluid control device 18 for supplying air and water and sucking liquids, and an inflator 19 for inflating the disposable protection cover such that the insertion section 11 of the endoscope 13 can be easily inserted into and removed from the disposable protection cover as will be explained later in detail. These devices are installed in a box 20 having casters. The video processor 15 and light source device 17 are coupled with the operation section 12 of the endoscope 13 by means of signal conductors and a light guide optical fiber bundle provided in a universal cord 21, and the fluid control device 18 is coupled with the conduit channels provided within the disposable protection cover by means of conduit tubes arranged along the universal cord 21. The construction and operation of the above mentioned devices except for the inflator 19 are well known in the art, so that the detailed explanation thereof is dispensed with.

The disposable protection cover of the present embodiment comprises an insertion section cover 22 for covering the insertion section 11 of the endoscope 13, an operation section cover 23 for covering the operation section 12 of the endoscope and a universal cord cover 24 for covering the universal cord 21. These disposable protection covers 22, 23 and 24 are formed separately from each other, and suitable coupling mechanisms are provided between junctions thereof in order to avoid a possible contamination through the junctions.

The protection covers 22, 23 and 24 may be made of various materials. For instance, flexible vinyl and rubber may be used as a soft material and rigid or semi-rigid plastics may be used as a hard material. It should be noted that the protection covers 22, 23 and 24 are not always necessary to be made of the same material, but may be made of different materials. For instance, the insertion section cover 22 may be made of flexible rubber, the operation section cover 23 may be made of rigid plastics and the universal cord cover 24 may be made of semi-rigid vinyl.

Prior to the actual examination, a set of protection covers is removed from a package and a connecting portion 25 made of rigid or semi-rigid plastics and provided at a proximal end of the insertion section cover 22 is hung from a cover supporting member 27 of a cover supporting device 26. In order to prevent the connecting portion 25 from being contaminated, the cover supporting member 27 may be covered with a disposable cover. As will be explained later, the connecting portion 25 of the insertion section cover 22 is utilized to couple the insertion section cover with the operation section cover 23.

A height of the cover supporting member 27 has to be adjusted such that when the insertion section cover 22 is hung from the cover supporting member 27, the distal end of the disposable insertion section cover is not brought into contact with a floor. However, if a height of the cover supporting member 27 is made too high, the inserting operation becomes difficult, so that the cover supporting member could not be made so high. In such a case, the insertion section cover 22 has to be supported by an operator.

After the insertion section cover 22 has been hung from the cover supporting member 27, an end of an air supply tube 28 connected to the inflator 19 is coupled with a nipple portion 29 provided in the connecting portion 25 of the insertion section cover 22, and then the inflator 19 is driven to supply air through the tube 28 into insertion section cover 22. In this manner, the insertion section cover 22 is inflator, so that the insertion section 11 of the endoscope 13 can be easily inserted into the insertion section cover 22. Then, the inflator 19 is de-energized and the tube 28 is decoupled from the nipple portion 29. The inflating operation is also performed upon removing the insertion section 11 from the insertion section cover 22. After the examination, the protection covers 22, 23 and 24 are discarded as medical waste and the endoscope is cleaned and sterilized after all examinations for one day have been finished.

Figure 2:
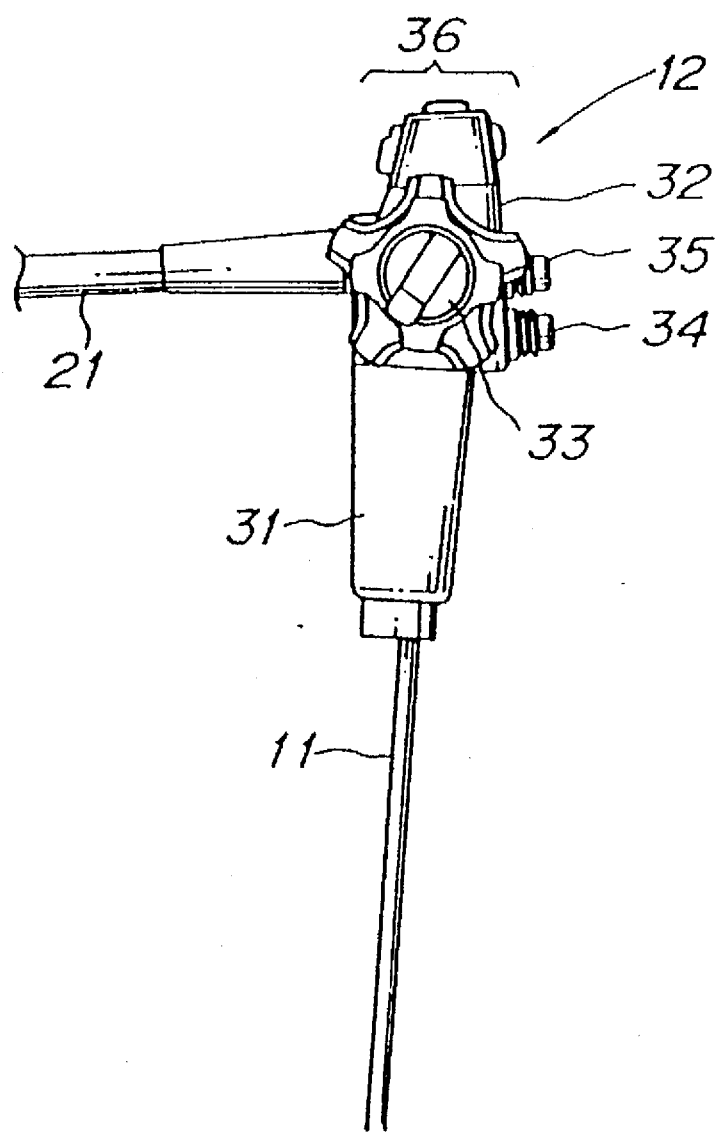
FIG. 2 is a front view illustrating the construction of the operation section of the endoscope shown in FIG. 1.

FIG. 2 shows the construction of the operation section 12 of the endoscope. To the operation section 12 are connected the insertion section 11 and universal cord 21. The operation section comprises a grip portion 31 and a main portion 32. The main portion 32 comprises angle knobs 33 for bending the distal end of the insertion section 11, air and water supply control switch 34, suction control switch 35 and function switch 36 for controlling the operation of a camera taking photographs of the object under inspection. In the present embodiment, the angle knobs 33 are detachably secured to the main portion 32 of the operation section 12. The angle knobs 33 may be of a disposable type and may be contained in a package in which the disposable protection cover is installed. Alternatively the angle knobs 33 may be reused after sterilization.

FIG. 3 is a perspective view illustrating the construction of the insertion section 11 of the endoscope. In the present embodiment, a lateral cross section of a distal end construction member 37 is semicircular and in a front surface 38 of the member 37 there are arranged outlets of a pair of illuminating optical systems, i.e. optical fiber bundles 39 and an observing optical system 40 provided between the illuminating optical systems.

Figure 5:
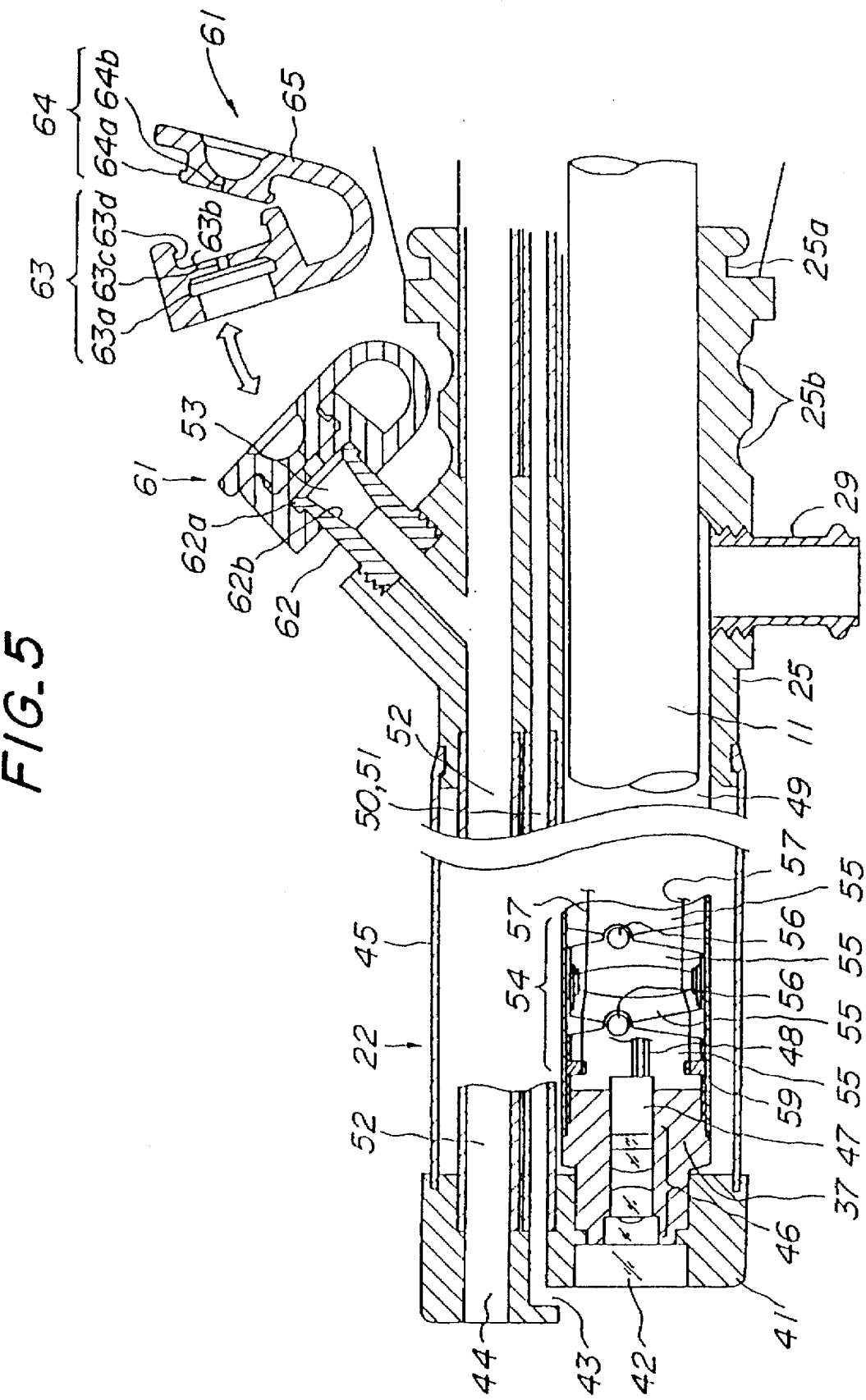
FIG. 5 is a longitudinal cross sectional view showing the endoscope system shown in FIG. 1.

FIG. 4 is a perspective view depicting the construction of a distal end of the insertion section cover 22 and FIG. 5 is a longitudinal cross sectional view showing the insertion section cover 22 into which the insertion section 11 of the endoscope is inserted. In a front surface of a distal end construction member 41 of the insertion section cover 22, there are provided a semicircular observation window 42 made of transparent material, a nozzle 43 for ejecting air and water toward the window 42, and an outlet opening 44 of a forceps channel 52. By ejecting the air water from the nozzle 43, the outer surface of the observation window 42 can be cleaned.

To the distal end construction member 41 of the insertion section cover 22, is connected one end of an insertion section cover tube 45 which isolates a main portion of the insertion section 12 from the outside. This cover tube 45 is made of a flexible material. In the present embodiment, the cover tube 45 is made of flexible rubber. The other end of the cover tube 45 is connected to the connecting portion 25 of the insertion section cover 22.

As illustrated in FIG. 5, within the distal end construction member 37 of the insertion section 11 which is faced with the observation window 42 of the distal end construction member 41 of the insertion section cover 22, there are arranged an observing lens system 46 for forming an image of an object under inspection and a solid state image sensor 47 for picking-up the image of an object under inspection. The solid state image sensor 47 is electrically connected to the video processor 15 (FIG. 1) by means of signal conductors 48 extending through the insertion section 11 and universal cord 21.

Within the insertion section cover 22, there are formed endoscope insertion channel 49 into which the insertion section 11 is inserted, an air supply conduit 50 communicated with the air and water ejecting nozzle 43, a water supply conduit 51 also communicated with the nozzle 43, and a forceps channel 52. These channels and conduits are arranged in parallel with each other. The forceps channel 52 is communicated with a forceps inlet opening 53 provided in the connecting portion 25 and is also communicated with the fluid control device 18 by means of a conduit tube provided within the universal cord 21. Therefore, the forceps channel 52 is sometimes called a suction channel. Further, the conduits 50 and 51 are also called conduit channels or conduit tubes in the present specification.

In order to bend the distal end of the insertion section 11 by operating the angle knobs 33 such that an optical axis of the observing optical system 46 is moved up and down as well as right and left, there is provided a bending portion 54 adjacent to the distal end construction member 37 of the insertion section 11 of the endoscope. The bending portion 54 comprises a series of nodal rings 55 which are coupled with each other by means of journal pins 56 and a front end ring is connected to the distal end construction member 37 of the insertion section 11. A pair of wires 57, 58 are secured to the front end ring 55 at diametrically opposing points. These wires 57, 58 are extended within the insertion section 11 and are wound around a pair of pulleys provided in the operation section 12. In FIG. 5, only the wire 57 is shown, but the other wire 58 is illustrated in FIG. 20. A series of nodal rings 55 is covered with a flexible rubber tube 59 in a liquid tight manner. By operating the angle knobs 33, the pulleys may be rotated and thus the wires 57, 58 may be moved so as to direct the distal end of the insertion section 11 into a desired direction. This construction is well known in the art, so that its detailed explanation may be dispensed with. At a proximal end of the connecting portion 25 there are formed a ring shaped recess 25a for connecting the operation section cover 23 and a ring shaped recesses 25b for engaging the connecting portion with the supporting member 27 in the supporting device 26.

According to the invention, the forceps inlet opening 53 communicates with the forceps channel 52 and is selectively closed by means of a forceps plug 61 made of resilient material. The forceps inlet opening 53 is formed by a tube 62 which is secured to the connecting portion 25 and includes a flange 62a and a tapered inner wall 62b. The forceps plug 61 is resiliently clamped on the flange 62a of the tube 62.

The forceps plug 61 comprises a first plug body 63, a second plug body 64 and an arm 65 for coupling said first and second plug bodies with each other. The first plug body 63 includes a first ring shaped recess 63a which is engaged with the flange 62a of the tube 62 forming the forceps inlet opening 53, a disk 63b having a central hole 63c whose diameter is smaller than a diameter of a forceps, and a second ring shaped recess 63d. The plug body 64 comprises a flange 64a which is resiliently inserted into the second ring shaped recess 63d of the first plug body 63 and a slit 64b formed at a center position.

As explained above, according to the invention, the forceps plug 61 is formed separately from the operation section cover 23 of the disposable protection cover, so that the forceps plug can be easily exchanged even during the examination. In this case, it is advantageous that the forceps plug 61 is formed such that it can be commonly used for various disposable protection covers for various endoscopes. Further, it is also advantageous to prepare a number of forceps plugs made of different materials having different rigidities or hardnesses.

In case of inserting the forceps, the forceps is inserted into the forceps inlet opening 53 through the slit 64b formed in the second plug body 64 and the central hole 63c of the first plug body 63. In this case, the central hole 63c is resiliently widened, so that the forceps can be firmly grasped by the forceps plug 61. If it is difficult to insert the tip of the forceps from the slit 64b, the second plug body 64 is removed from the first plug body 63 to expose the central hole 63c. Then, the forceps can be easily inserted from the central hole 63c. Further, when a tip of a syringe for supplying a liquid into the cavity is inserted into the forceps inlet opening 53, the forceps plug 61 is removed from the tube 62.

FIGS. 6A to 6D show various insertion section covers having different constructions. That is to say, at least one of a diameter of the forceps channel 52, a length of the insertion section cover 23 and a diameter of the insertion section channel 49 is different from one another. The insertion section covers shown in FIGS. 6A and 6B have different diameters of the forceps channel 52, the insertion section covers of FIGS. 6A and 6C have different diameters of the insertion section inserting channel 49, and the insertion section covers illustrated in FIGS. 6A and 6D have different lengths. However, all the insertion section covers have a forceps inlet opening 53 having the same construction and therefore, the forceps plug 61 can be commonly used for these insertion section covers. Further it is preferable to prepare a plurality of forceps plugs having different rigidities. Moreover, FIGS. 6A to 6D show that at least one of the ring shaped recess 25a for connecting the operation section cover 23 to the insertion section cover 22, the ring shaped recesses 25b for securing the insertion section cover to the supporting member 27 and the nipple portion 29 for connecting the inflating tube 28 to the insertion section cover is commonly constructed for different insertion section covers. In this case, a diameter of other conduit channels may be used as a common parameter.

The insertion section covers shown in FIGS. 6A and 6B have ring shaped recesses 25a and 25b of the same construction, but have nipple portions 29 having different constructions. The insertion section covers of FIGS. 6A and 6C have the recesses 25a and nipple portions 29 of the same construction, but have recesses 25b of different constructions. The recesses 25b and nipple portions 29 of the insertion section covers of FIGS. 6A and 6D have the same construction, but the recesses 25a of these covers are different from each other. By constructing the disposable protection cover in the manner explained above, it is possible to avoid contamination and damage due to erroneous combinations.

FIG. 7 is a perspective view showing an embodiment of the forceps inlet opening. In the present embodiment, the forceps inlet opening is formed by a lure lock type fitting 65, so that various adaptors other than the syringe may be coupled with the forceps inlet opening. The remaining construction of the present embodiment is same as that of the previous embodiment, so that the forceps plug can be detachably secured to the forceps inlet opening during the examination.

Figure 8:
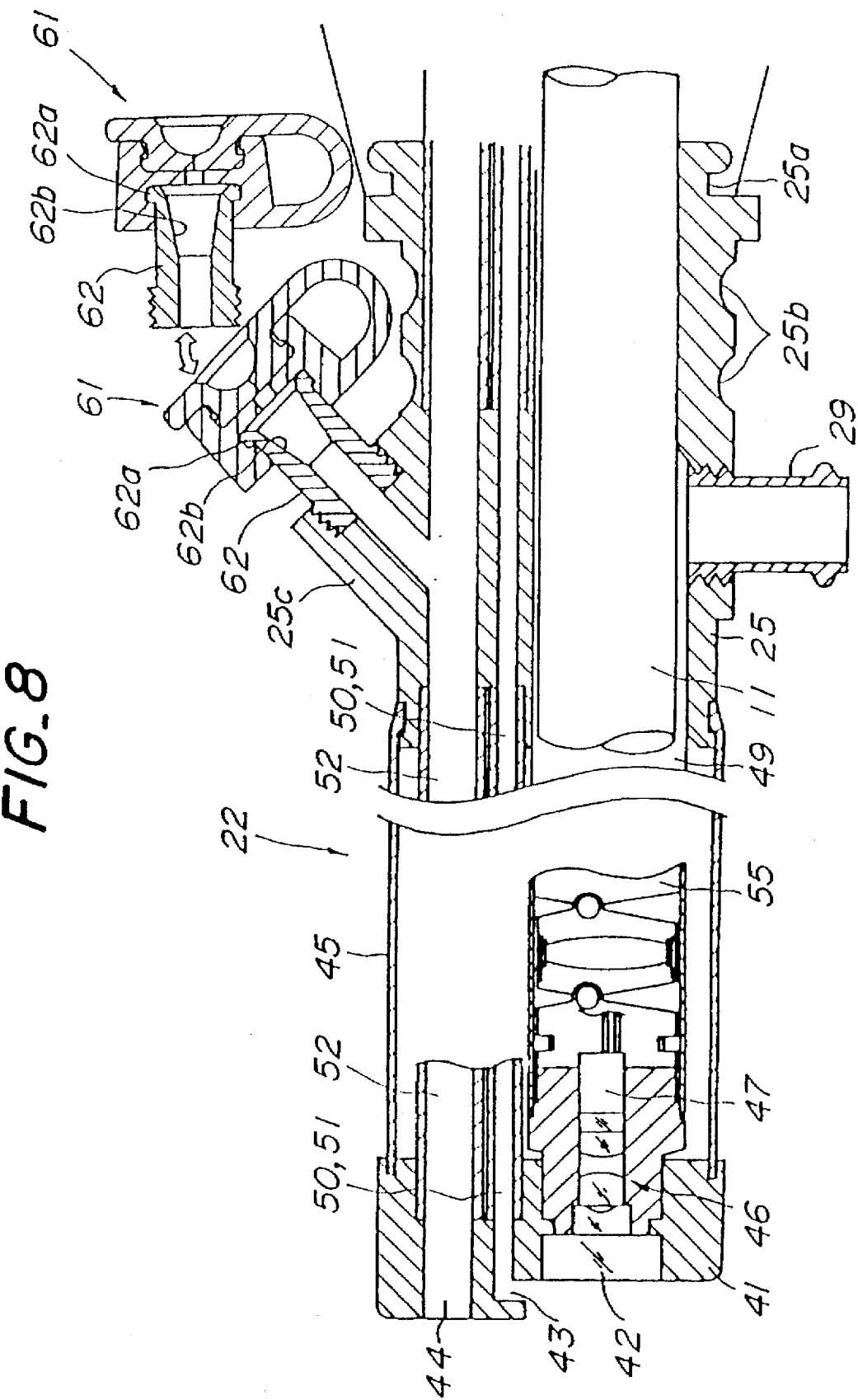
FIG. 8 is a cross sectional view showing another embodiment of the forceps plug according to the invention.

FIG. 8 is a cross sectional view showing another embodiment of the endoscope system according to the invention. In the present embodiment, the forceps plug 61 and the tube 62 for defining the forceps inlet opening 53 are secured to each other and the assembly of the forceps plug 61 and tube 62 is detachably screwed into a forceps inlet duct 25c formed in the connecting portion 25 of the insertion section cover 22.

Figure 9:
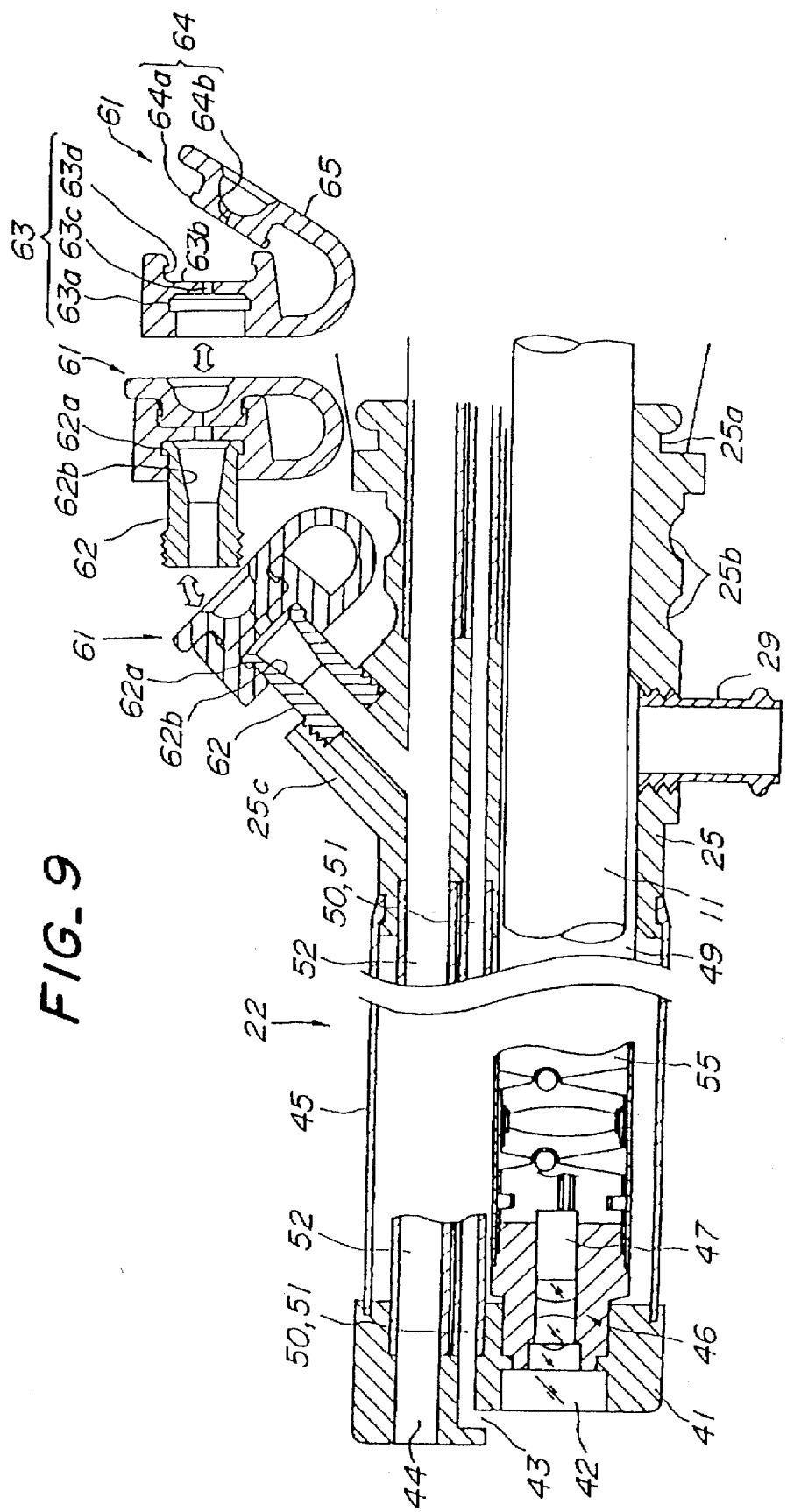
FIG. 9 is a cross sectional view showing another embodiment of the forceps plug according to the invention.

FIG. 9 is a cross sectional view illustrating a modification of the embodiment shown in FIG. 8. In the present embodiment, the forceps plug 61 is not permanently secured to the tube 62, but is detachably coupled with the tube 62.

As stated above, when the forceps is inserted into the forceps channel through the forceps plug 61, the forceps is resiliently clamped by the central hole 63c of the forceps plug. In this case, preferable clamping forces are different for respective forceps. For instance, in the case of using a canulation tube for E RCP (retrograde biliarytract image contrast), it is necessary to move a tip of the tube forward and backward slightly, so that the rather weak clamping force is desired. However, in the case of using an exploratory excision forceps, it is desired to obtain a strong clamping force. Therefore, it is advantageous to prepare a plurality of forceps plugs which can generate different clamping forces.

Figure 10:
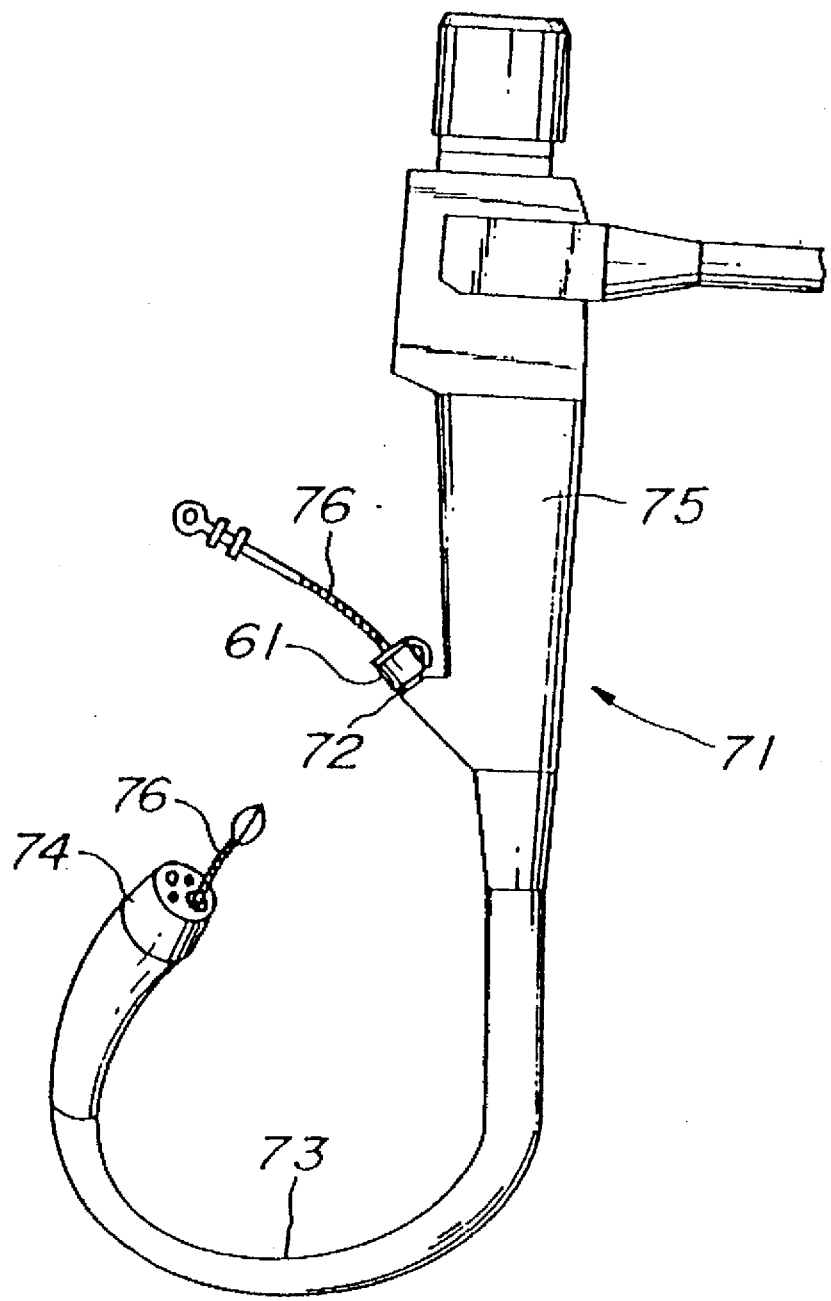
FIG. 10 is a front view illustrating the normal without-cover endoscope to which the forceps plug is secured.
Figure 11:
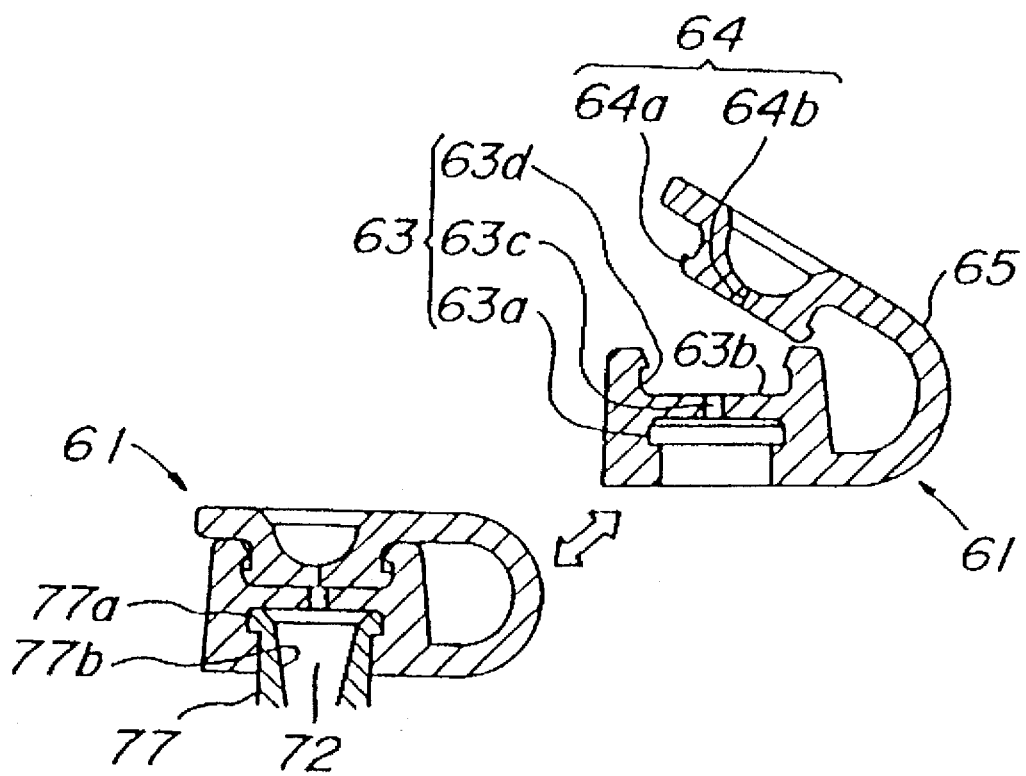
FIG. 11 is a cross sectional view depicting the forceps plug shown in FIG. 10.
Figure 12:
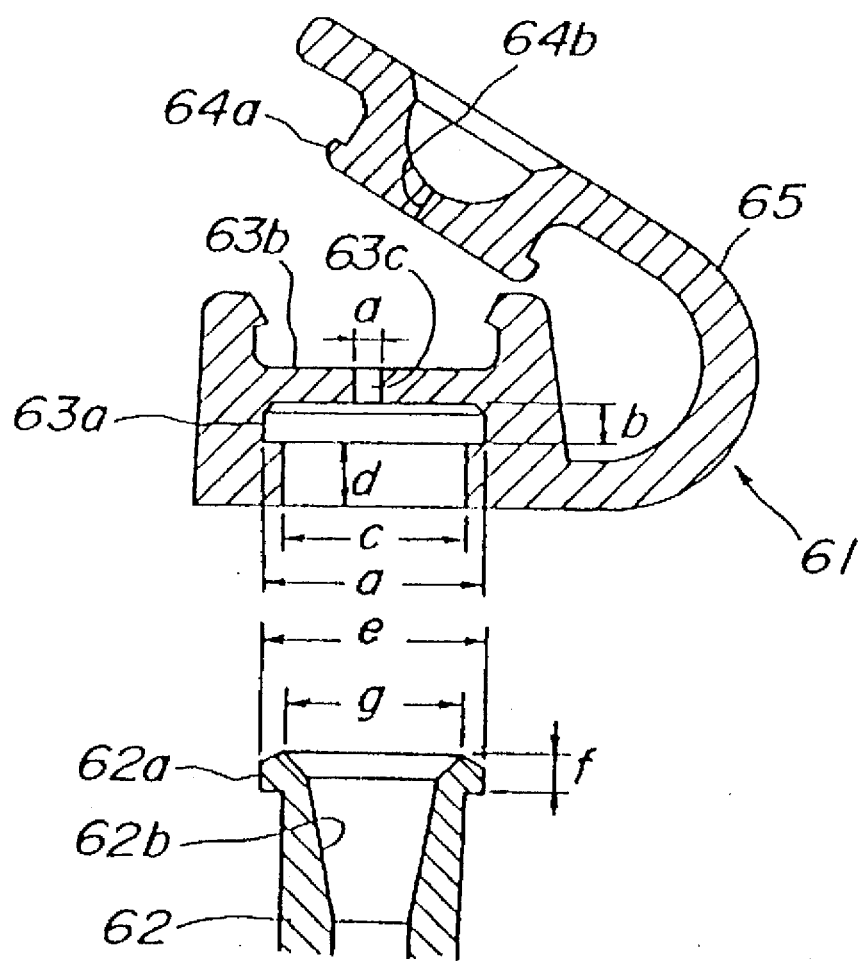
FIG. 12 is a cross sectional view showing the forceps plug according to the invention.

FIGS. 10 to 12 show another embodiment of the endoscope system according to the invention. In the present embodiment, the forceps plug may be used to close a forceps inlet opening provided on an ordinary endoscope which is used without the disposable protection cover. In the present specification, this ordinary endoscope is called a without-cover (coverless) endoscope when it is necessary to distinguish it from the above mentioned endoscope which is used with the disposable protection cover. The latter endoscope is then termed as a with-cover endoscope.

As illustrated in FIG. 10, a forceps plug 61 is detachably secured to a forceps inlet opening 72 of a without-cover endoscope 71 which comprises an insertion section 73 having a distal end 74 and an operation section 75. The without-cover endoscope 71 is well known in the art, and its detailed construction is not explained. A forceps 76 is inserted into a forceps channel formed within the insertion section 73 through the forceps plug 61 and its distal end is projected from the distal end 74 of the insertion section. In the present embodiment, the without-cover endoscope 71 is of the fiber scope type, but according to the invention, it may be of the electronic scope.

As shown in FIG. 11, the forceps inlet opening 72 is constructed by a cylindrical member 77 having a flange 77a and a tapered opening 77b. According to the Japanese Industrial Standard (JIS) T1301, the taper angle is defined to 6/10. The forceps plug 61 is the same as that shown in FIG. 5. A diameter of the central hole 63c is 1.3 mm and a length of the slit 64b is 2.4 mm. A diameter of the ring shaped recess 63a is smaller than a diameter of the flange 77a by about 8%, so that the forceps plug 61 is firmly coupled with the cylindrical member 77 and the forceps plug is hardly removed from the cylindrical member upon removing the forceps 76 from the forceps channel through the forceps plug. The forceps plug 61 is preferably made of silicon rubber having a hardness of 40°±3° in accordance with JIS A-hardness.

FIG. 12 shows dimensions of various parts of the forceps plug 61. A diameter a of the ring shaped recess 63b which has been used for the ordinary without-cover endoscope is 9.6 mm and a height b of the recess 63b is 1.8 mm. Sizes c and d of the forceps plug 61 are 7 mm and 3 mm, respectively. The forceps plug 61 is made of silicon rubber having a JIS A-hardness of 40°. The forceps inlet opening 53 of the insertion section cover 23 may be formed such that a diameter e of the flange 62a is 9.6–9.9 mm, a height f of the flange is 1.8 mm and a diameter g of the opening is 7.6 mm. Dimensions of the remaining portions are not defined. Further the cylindrical member 62 may be made of any suitable material. For instance, the cylindrical member 62 may be made of plastics or metals. In the present embodiment, the inner wall 62b of the cylindrical member is tapered so that the syringe can be easily and positively secured to the cylindrical member.

As explained above, in the present embodiment, the forceps plug 61 can be commonly used for the without-cover endoscope as well as the disposable protection cover, and thus the selection of the forceps plug can be performed easily and correctly.

Figure 13:
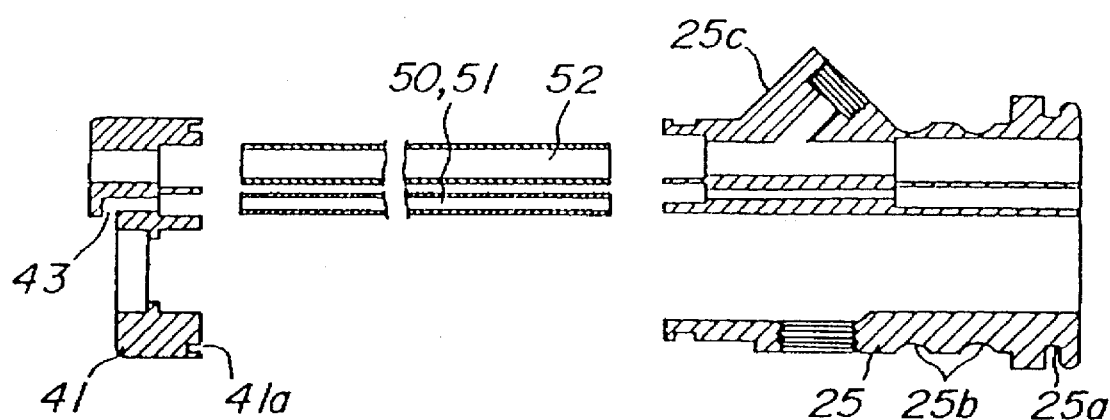
FIG. 13 is a cross sectional view illustrating a first step of manufacturing the operation section cover.
Figure 14:
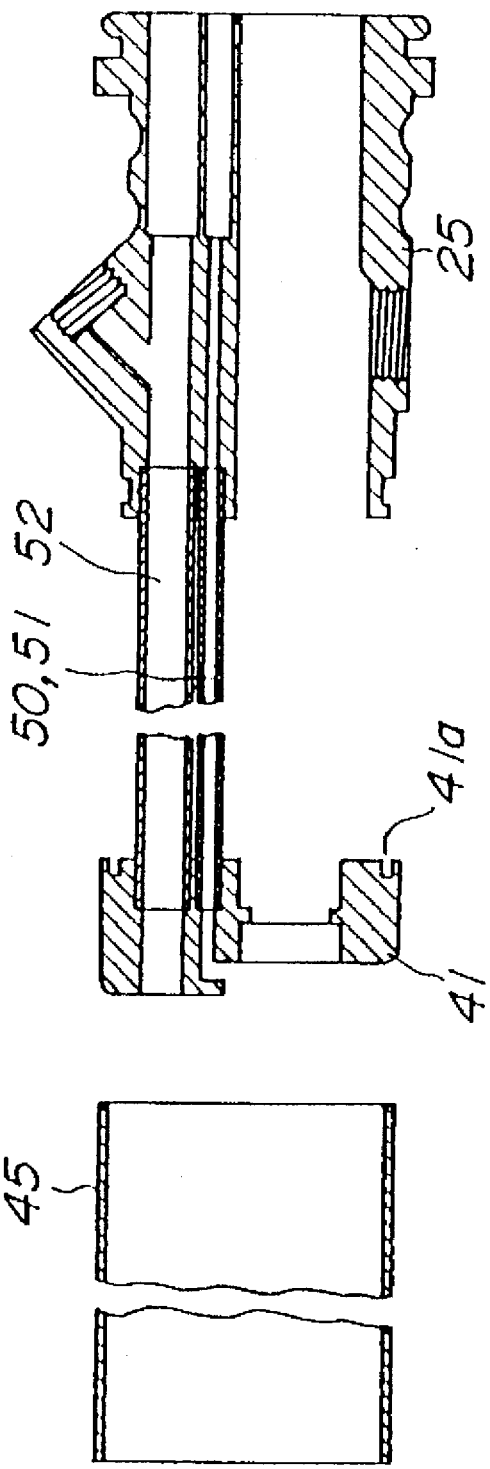
FIG. 14 is a cross sectional view depicting a second step of manufacturing the insertion section cover.
Figure 15:
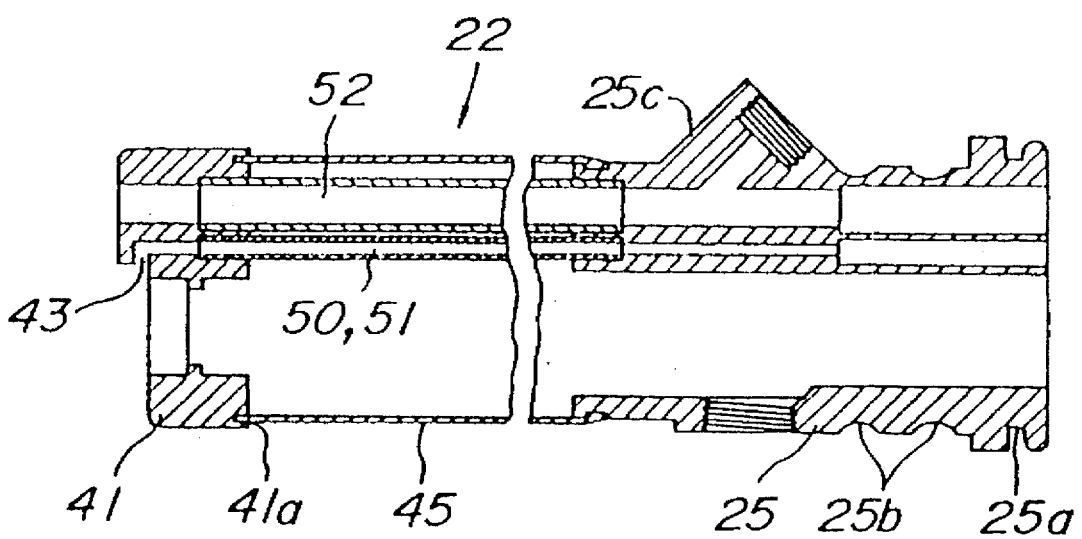
FIG. 15 is a cross sectional view showing a final step of manufacturing the insertion section cover.

FIGS. 13 to 15 show successive steps for manufacturing the disposable protection cover. This method comprises a first step for coupling first ends of the conduit tubes 50 to 52 with the distal end construction member 41 and coupling the other ends of the conduit tubes with the connecting portion 25 as shown in FIG. 14. These ends of the conduit tubes 50 to 52 can be hermetically secured with the aid of an adhesive agent. The method further comprises a second step for inserting the assembly of the conduit tubes 50 to 52, distal end construction member 41 and connecting portion 25 into the outer tube 45 and then one end of the rubber tube is secured to the distal end construction member 41 and the other end of the rubber tube is secured to the connecting portion 25. In this case, the one end of the rubber tube 45 is inserted into a recess 41a formed in the distal end construction member 41 and is secured thereto by adhesive agent. In this manner, the disposable protection cover for covering the insertion section of the endoscope can be manufactured in a simple manner. Further, any undesired projection is not formed on the outer surface of the protection cover, so that the cavity of patient can be effectively prevented from being injured.

Figure 16:
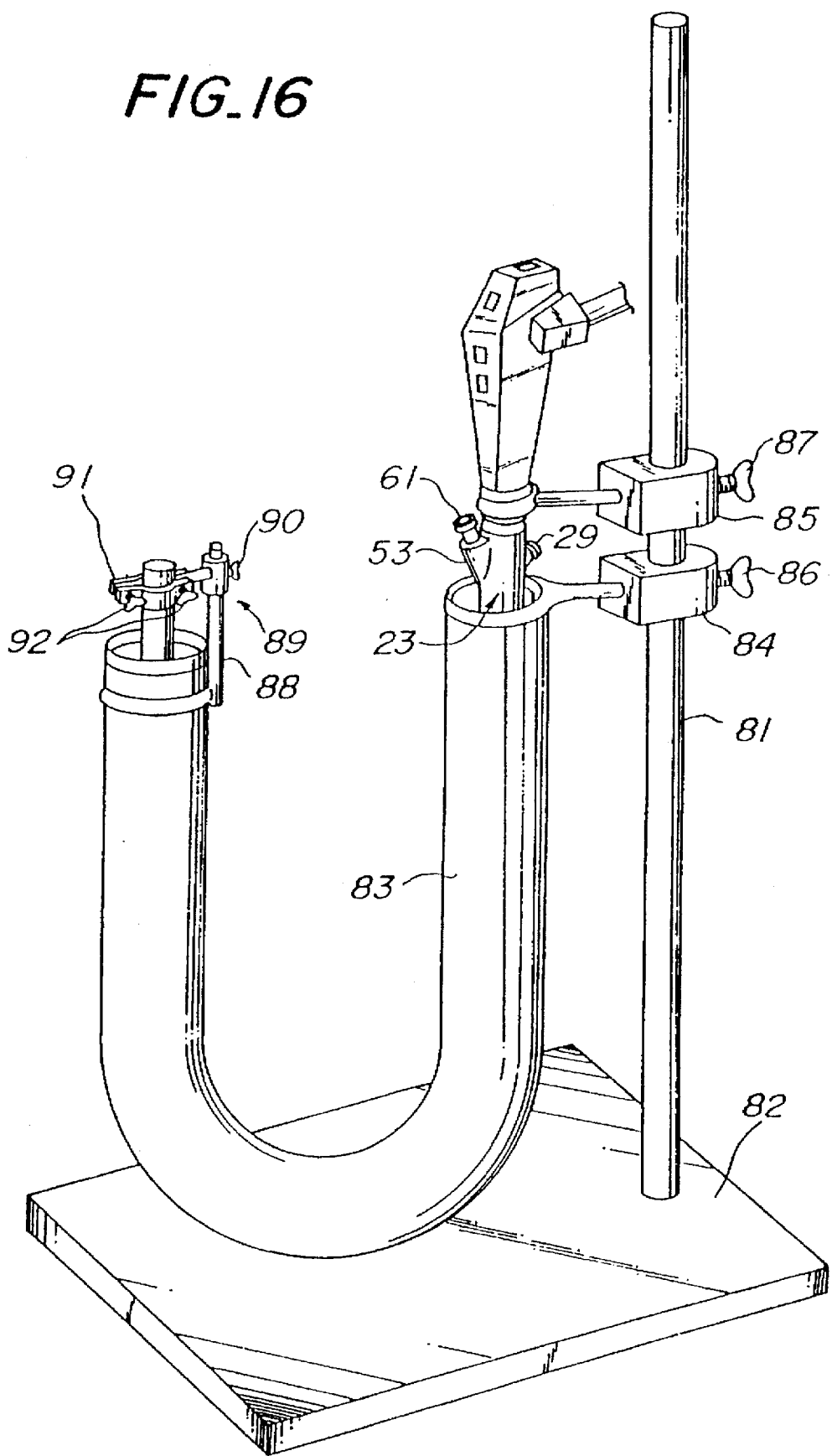
FIG. 16 is a perspective view illustrating the device for discarding the insertion section cover.

FIG. 16 is a perspective view showing a manner of discarding the used disposable protection cover by using a discarding apparatus. The discarding apparatus comprises a U-shaped tube, a first supporting device for supporting one end of the U-shaped tube, a stand for supporting the supporting device, a second supporting device for supporting the disposable protection cover at a level which is above a level at which said first supporting device supports the U-shaped tube, and a third supporting device for supporting the distal end portion of the disposable protection cover which protrudes from the other end of the U-shaped tube. In case of using a long protection cover, the distal end of the cover might be brought into contact with the floor. In order to avoid such a drawback, the discarding apparatus comprises the U-shaped tube.

As illustrated in FIG. 16, the discarding apparatus includes a stand 81 secured to a base plate 82, and a U-shaped tube 83. A U-shaped tube supporting device 84 and a protection cover supporting device 85 are provided on the stand 81 such that the device 85 is situated above the device 84. Positions of these devices 84 and 85 on the stand 81 can be changed by operating screws 86 and 87, respectively. One end of the U-shaped tube 83 is supported by the supporting device 84 and the connecting portion of the insertion section cover 22 is supported by the supporting device 85. At the other end of the U-shaped tube 83, there is provided a post member 88 to which a supporting device 89 is secured such that a height of the post member can be adjusted by operating a screw 90. The supporting device 89 includes a fitting means 91 for supporting the distal end portion of the insertion section cover 22 by operating screws 92.

After the examination, the insertion section 11 of the endoscope covered with the insertion section cover 22 is inserted into the U-shaped tube 83 from its one end. Then, the connecting portion 25 of the insertion section cover 23 is supported by the supporting device 85. In this case, the recesses 25b formed on the outer surface of the connecting portion 25 may be advantageously utilised. Then, the distal end portion of the insertion section cover projecting from the other end of the U-shaped tube 83 is clamped by the fitting means 91. The inflating tube 28 is connected to the nipple portion 29 on the connecting portion 25 to inflate the insertion section inserting channel 49. In this condition, the insertion section 11 of the endoscope is removed from the insertion section inserting channel 49 of the insertion section cover 22. In this manner, the used insertion section cover 22 can be discarded. During this operation, there is no fear that the insertion section cover 23 is brought into contact with the floor and the insertion section 11 of the endoscope can be removed form the insertion section cover 22 of the protection cover in an easy and safe manner.

FIGS. 17 to 19 show several embodiments of the conduit channels formed in the form of a multilumen tube at both ends thereof which are secured to the distal end construction member 41 and the connecting portion 25, respectively. In the embodiment shown in FIG. 17, a multilumen tube 101 is formed symmetrically with respect to an axis Y. In the embodiment illustrated in FIG. 18, a multilumen tube 102 is shaped symmetrical with respect to X and Y axes, and in the embodiment shown in FIG. 19 a multilumen tube 103 is formed symmetrically with respect to a center point O.

By constructing the multilumen tubes 101 to 103 symmetrically as depicted in FIGS. 17 to 19, they may be assembled in any directions with respect to the distal end construction member and connecting portion of the insertion section cover. That is to say, any end of the multilumens may be secured to the distal end construction member 41 as well as to the connecting portion 25. Further, the multilumen tubes 102 and 103 may be rotated by 180° about its longitudinal axis. Therefore, the manufacture of the disposable protection cover becomes easy. In these embodiments, the conduit channel tubes 50 to 52 are formed as the multilumen tube at both ends thereof. However, these conduit channel tubes may be formed as the multilumen tube over the whole length or a plurality of multilumen tube portions may be provided along the whole length of the insertion section cover. Further, the tubes within the universal cord 21 may be also formed as the multilumen tube.

FIGS. 20 and 21 are cross sectional views showing insertion section covers having the multilumen tubes 101 and 102 shown in FIGS. 17 and 18, respectively, in which the insertion section of the endoscope is inserted. The cross section is cut at the bending portion 54 of the insertion section cover 22 at which the multilumen tube is provided. Each of the multilumen tubes 101 and 102 is arranged within the rubber tube 45 at its upper half, and the insertion section 11 of the endoscope having the substantially semicircular cross section is inserted in the lower half portion within the rubber tube 45. In the bending portion 54 of the insertion section, there are arranged a plurality of nodal rings 55 each of which is formed by a blade 55a and rubber sheets 55b, 55c applied on both surfaces of the blade. Within the nodal rings 55, there are arranged light guide optical fibers 39, signal conductors 48 and wires 57 and 58.

As shown in FIGS. 20 and 21, the conduit channels 50 to 52 constructed as the multilumen tube 101, 102 are arranged in an upper half within the rubber tube 45 and the insertion section 11 of the endoscope is arranged in a lower half. According to the invention, in order to bend the bending portion 54 of the insertion section 11 of the endoscope in a symmetrical manner, the bending portion is constructed such that a radius of curvature of the bending portion bent in the downward direction in FIGS. 20 and 21 is smaller than a radius of curvature of the bending portion in the upper direction. Then, when the insertion section 11 of the endoscope is inserted into the insertion section cover 22, the distal end of the assembly of the endoscope and protection cover can be bend in a substantially symmetrical manner.

Figure 22A:
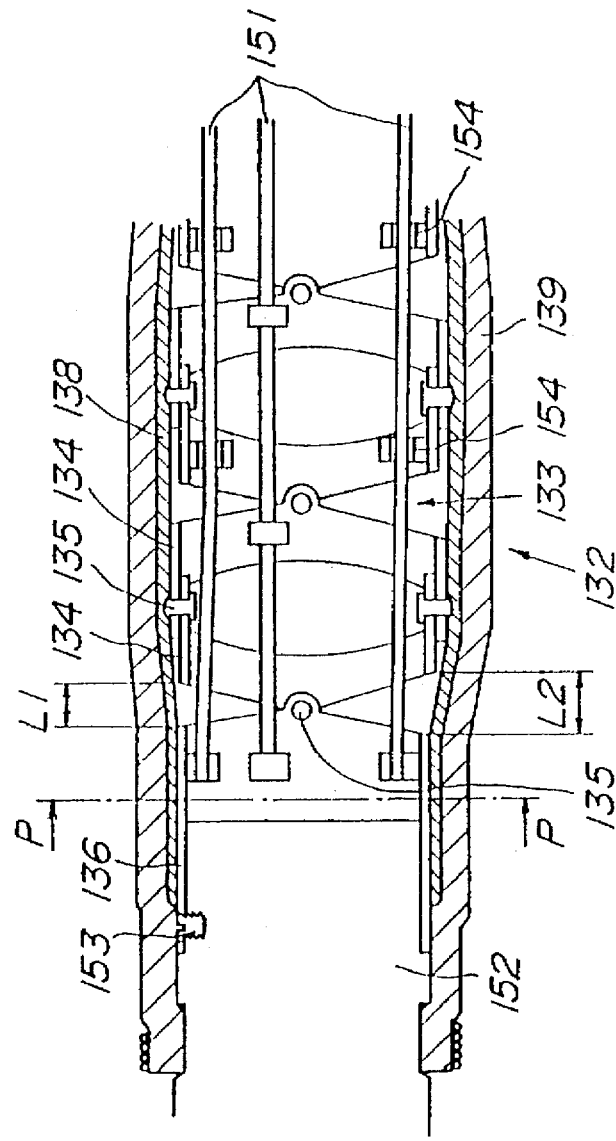
FIGS. 22A and 22B are cross sectional views illustrating an embodiment of the bending portion in the insertion section according to the invention.
Figure 22B:
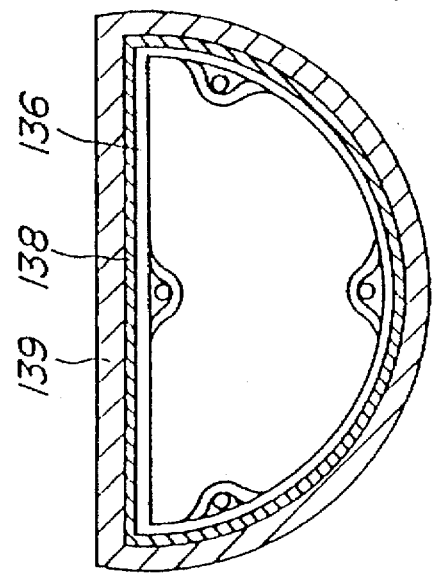

FIG. 22A is a cross sectional view depicting an embodiment of the bending portion of the insertion section of the endoscope for use with the disposable protection cover, and FIG. 22B is a cross sectional view cut along line P—P in FIG. 22A. A bending portion is generally denoted by a reference numeral 132. The bending portion 132 is formed by a bending tube 133 including a plurality of nodal rings 134, journal pins 135 for coupling the nodal rings, blade 138, four wires 151 and wire supports 154 secured on inner walls of the nodal rings by soldering. A front nodal ring 136 is secured to a distal end construction member 152 by means of screws 153. To an inner wall of the front nodal ring 136 are secured ends of the wires 151 by means of soldering. The wires 151 are mechanically coupled with the angle knobs 33 shown in FIG. 2.

The blade 138 is formed by fine metal wires and is arranged on the nodal rings 134. One end of the blade 138 is secured to the outer wall of the front nodal ring 136 by soldering and the other end of the blade is secured to another end nodal ring (not shown) also by soldering. The blade 138 is covered with a rubber tube 139 having one end is connected to the distal end construction member 152 by a string and another end also secured to a flexible tube also by a string in a liquid tight manner.

As is well known, the wires 151 are extended within the insertion section up to the operation section 12 on which the angle knobs 33 are provided. One of the angle knobs 33 is an up and down angle knob and the other is a right and left angle knob, and these angle knobs are secured to coaxially arranged shafts. These shafts are coupled with sprockets and chains connected to the wires 151 are wound around the sprockets. Therefore, by rotating the angle knobs 33, the wires 151 can be moved and thus a series of the nodal rings 134 can be bent in the up and down directions as well as in the right and left directions.

Figure 23:
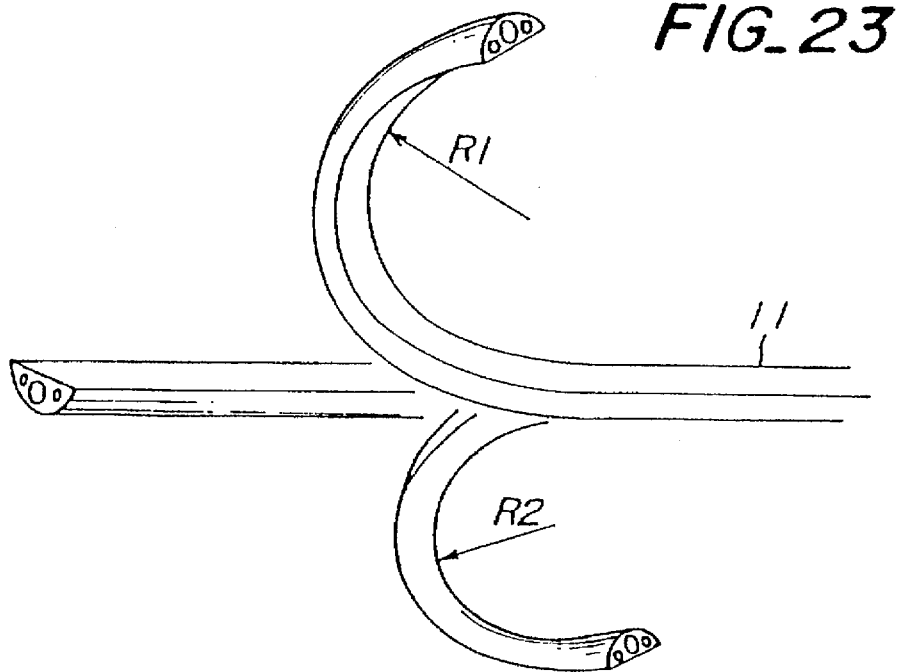
FIG. 23 is a perspective view illustrating the bending movement of the insertion section.
Figure 24:
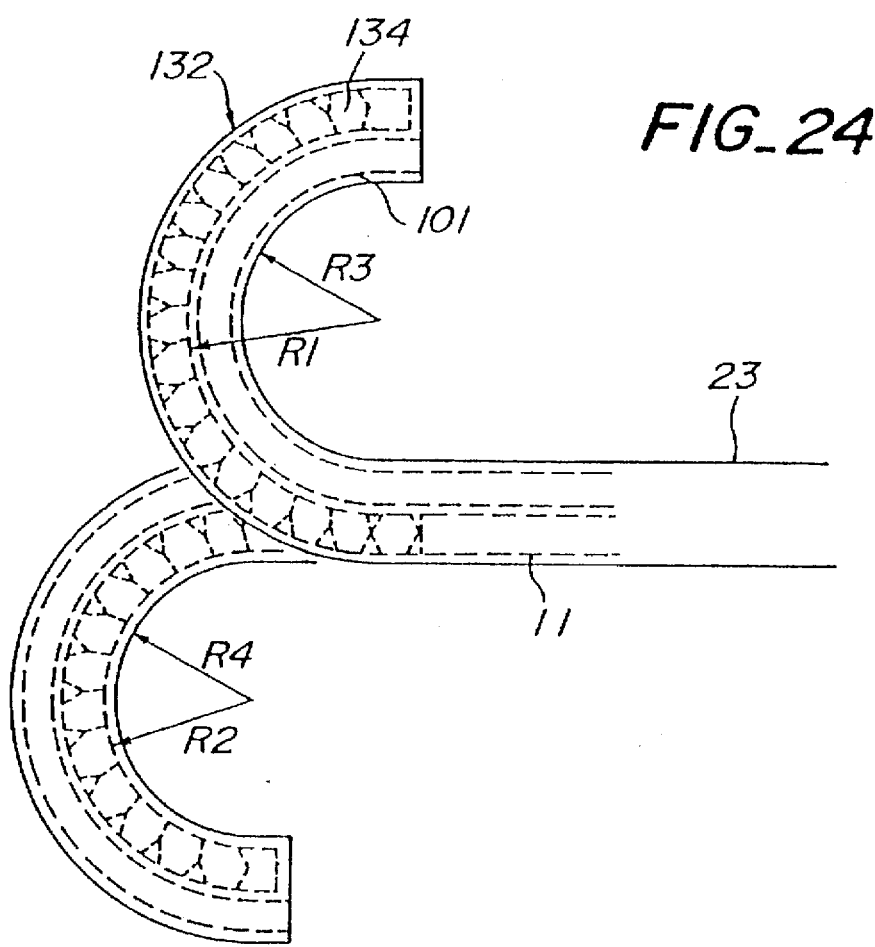
FIG. 24 is a schematic view representing the bending movement of the assembly of the endoscope and protection cover.

Now it is defined that a length between shoulders of successive nodal rings 134 is termed as a shoulder space. Then a radius of curvature of the bending movement of the bending portion 132 is determined by the shoulder space, because the nodal rings 134 can be rotated until adjacent shoulders of the nodal rings are brought into contact with each other. In the present embodiment, the shoulder space L1 of upper portions of the nodal rings 134 is set smaller than the shoulder space L2 of lower portions of the nodal rings. It should be noted that the shoulder space L1 defines the radius of curvature R1 of the upward bending movement of the bending portion and the shoulder space L2 limits the radius of curvature R2 of the downward bending movement of the bending portion, so that the radius of curvature of the downward bending movement becomes smaller that that of the upward bending movement (R2<R1) by setting L1<L2. This is clearly shown in FIG. 23. Then, as illustrated in FIG. 23, a radius of curvature R3 of the upward bending movement of the assembly of the insertion section 11 of the endoscope and the insertion section cover 22 becomes substantially equal to a radius of curvature R4 of the downward movement of the assembly. It should be noted that it is not always necessary to form all the nodal rings 134 to satisfy the above mentioned relationship of L1<L2, but some nodal rings may be formed such that the upper shoulder space L1 is substantially identical with the lower shoulder space L2.

For instance, when the bending portion of the insertion section of the endoscope having the maximum upward and downward bending angles set to 210° and 90°, respectively is bent by upward and downward bending angles of 45°, only a proximal portion of the bending portion is bent, but a distal end portion is not substantially bent. In such a case, it is preferable to bend the assembly of the insertion section and the insertion section cover symmetrically in both the upward and downward directions.

FIGS. 25A and 25B show another embodiment of the insertion section of the endoscope for use with the disposable protection cover according to the invention. In the present embodiment, the shoulder space L1 of the upper portion of the nodal rings 134 is set to be equal to the shoulder space L2 of the lower portion of the nodal rings, but the journal point line connecting the journal pins 135 is deviated from a central axis line A by a distance Y in a downward direction. The center axial line A can be defined such that distances y from the line to the upper and lower inner surface of the nodal rings 134 are identical with each other. Also in this case, the radius of curvature R1 of the upward bending movement of the insertion section of the endoscope can be larger than the radius of curvature R2 of the downward bending movement.

FIGS. 26A and 26B show still another embodiment of the insertion section of the endoscope for use in the endoscope system according to the invention. In the present embodiment, the shoulder spaces L1 and L2 are set to be identical with other and the journal pins 135 are arranged on the center axial line, but a thickness T of the rubber tube 139 at a upper portion is set to be thicker that a thickness t of the rubber tube at a lower portion (t<T). By constructing the bending portion in such a manner, it is possible to make the radius of curvature R1 in the upward bending movement of the insertion section larger than the radius of curvature R2 on the downward bending movement of the insertion section. Therefore, in the assembly of the insertion section of the endoscope and the insertion section cover of the disposable protection cover, the upward bending movement and the downward bending movement can be made substantially identical with each other. In other words, the distal end of the assembly can be bent symmetrically by operating the angle knobs provided on the operation section of the endoscope and to improve the operating faculty.

FIG. 27 depicts still another embodiment of the insertion section of the endoscope for use in the endoscope system according to the invention. Also in the present embodiment, the bending portion of the insertion section is constructed such that the radius of curvature R1 is larger than the radius of curvature R2 by any means shown in FIGS. 22 to 26. Further in the present embodiment, the forceps channel is formed such that a radius of curvature R5 of the forceps channel in the upward bending movement of the assembly becomes identical with a radius of curvature R6 of the forceps channel when the assembly is bent in the downward direction. By constructing the insertion section cover in the above mentioned manner, the forceps is subjected to the substantially same resistance in the both bending movements, and the multilumen tube is subjected to the substantially same compression force and is stabled.

Figure 28:
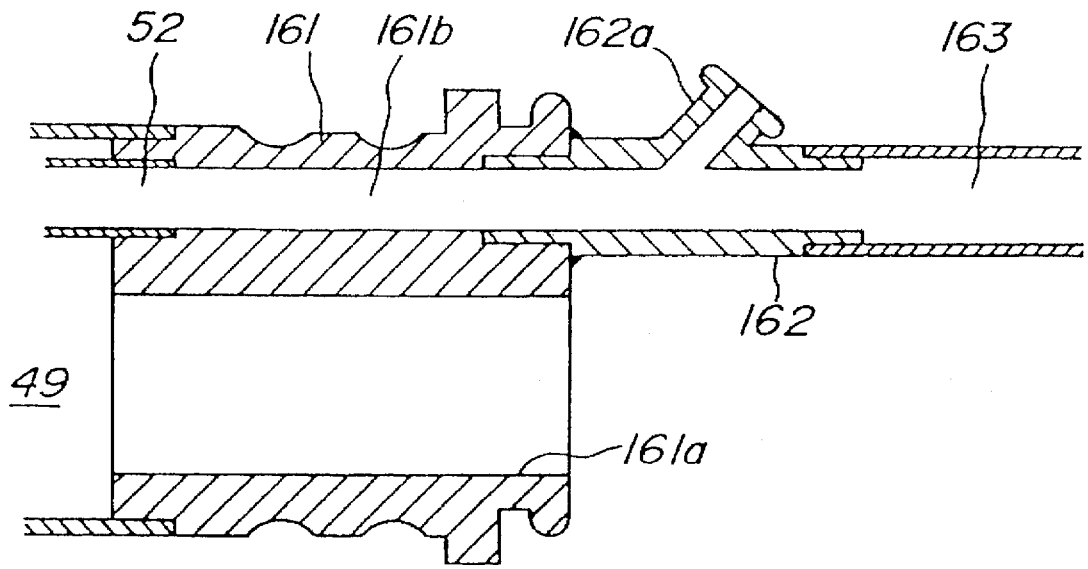
FIG. 28 is a cross sectional view representing another embodiment of the connecting portion of the insertion section cover according to the invention FIG. 29 a side view of the connecting portion shown in FIG. 28.
Figure 29:
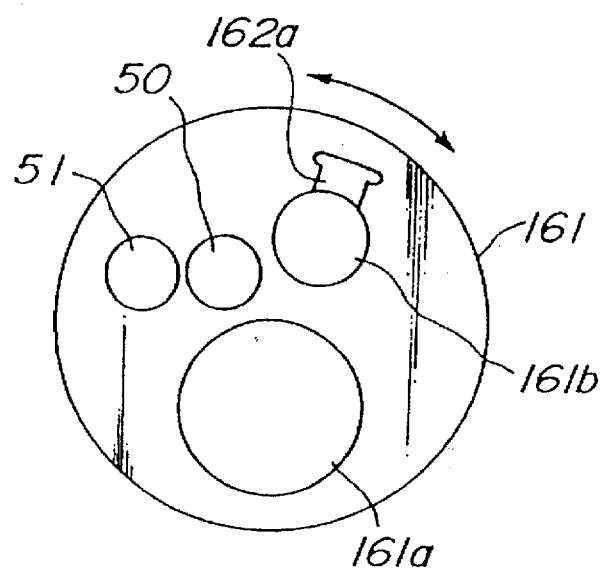

FIGS. 28 and 29 illustrate another embodiment of the insertion section cover of the disposable protection cover according to the invention. In the present embodiment, the forceps inlet opening is not provided in the connecting portion of the insertion section cover, but a separate tube having the forceps inlet opening formed therein is inserted into a proximal end face of the connecting portion. A connecting portion 161 has formed therein an insertion section inserting hole 161a communicated with the insertion section inserting channel 49, and a forceps conduit 161b communicated with the forceps channel 52. To the proximal end of the forceps conduit 161b is secured a tube-like member 162 having a forceps inlet opening 162a to which the forceps plug may be detachably secured. To a proximal end of the tube-like member 162 is secured a flexible tube 163 which is connected via the universal cord to the suction device in the external endoscope apparatus shown in FIG. 1. The tube-like member 162 may be secured to the connecting portion 161 by means of adhesive agent or thermal fusing. As shown in FIG. 29, in the connecting portion 161 there is provided the air supply conduit 50 and the water supply conduit.

In the present embodiment, upon assembling the connecting portion 161 and tube-like member 162, the angular position of the forceps inlet opening 162a can be adjusted at will as represented by a double-headed arrow in FIG. 29 in accordance with a requirement of users.

FIGS. 30A, 30B and 31 show another embodiment of the operation section cover of the disposable protection cover according to the invention for use with the fiber scope type endoscope. An operation section 171 of the fiber scope comprises angle knobs 172, various switches 173 and an eyepiece 174. An operation section cover comprises main body halves 175a, 175b and a eyepiece cover portion 175c. As shown in FIG. 31, these main body halves 175a, 175b and eye piece cover portion 175c are coupled with each other by means of pins 176 and holes 177 formed in edges of these portions. Further, in main body halves 175a, 175b, there are formed semicircular recesses 178 for defining an aperture through which the shafts are protruded from the operation section cover. The angle knobs 172 are detachably secured to the shafts.

In the eyepiece cover portion 175c there is provided a dioptry adjusting lens 179. It should be noted a plurality of eyepiece cover portions having different dioptries are prepared and any one of them having a desired dioptry adjusting lens is selected in accordance with a dioptry of an operator. Alternatively, a plurality of dioptry adjusting lenses having different dioptries are prepared and any desired one of them may be detachably secured to the eyepiece cover portion 175c. Moreover, the eyepiece cover portion 175c may be formed integrally with one of the main body halves 175a, 175b. In this case, the dioptry adjusting lens 179 may be detachably secured to the eyepiece cover portion 175c.

The present invention further proposes a novel endoscope system in which conduit tubes extending from the operation section cover 23 are fixed such that the protection cover is not contaminated by the contact with the conduit tubes. Several embodiments of such endoscope system will be explained.

FIG. 32 shows an embodiment of the endoscope system having conduit tube fixing means. Portions of the present embodiment similar to those of the previous embodiments are denoted by the same reference numerals used in the previous embodiments and a detailed explanation thereof is dispensed with. In FIG. 32, the conduit tubes are generally denoted by a reference numeral 201. These conduit tubes are extending from the operation section cover 23 of the disposable protection cover and are fixed to the operation section 12 of the endoscope, the universal cord 21 and a connector 202 by means of fixing members 203, 204 and 205. As shown in FIG. 32, these conduit tubes 201 are covered with the universal cord cover 24 together with the universal cord 21. The signal conductors within the universal cord 21 are coupled with the video processor 15, the light guide optical fiber bundle is coupled with the light source device 17 and the conduit tubes 201 are connected to the fluid control device 18.

FIGS. 33 to 41 show several embodiments of the fixing member 203. The conduit tubes include an air supply tube 211 communicated with the air supply channel 50, a water supply tube 212 communicated with the water supply channel 51 and a suction tube 213 communicated with the suction channel, i.e. forceps channel 52.

In an embodiment shown in FIG. 33, a fixing member 210 comprises a base portion 210a secured to the outer surface of the operation section 12 of the endoscope, a cover portion 210b and a snap fit portion 210c. These portions 210a, 210b and 210c are formed integrally as a unit member and are made of resilient material.

In an embodiment illustrated in FIG. 34, a fixing member 220 comprises a so-called magic tape 220a. In an embodiment depicted in FIG. 35, a fixing member 222 includes a permanent magnet 222a and a ring 222b made of magnetic material. The tubes 211 to 213 are inserted into the ring 222b and the ring is fixed to the permanent magnet 22a. In an embodiment shown in FIG. 36, a fixing member 224 comprises a pair of strings 224a and 224b whose one ends are secured to the outer surface of the operation section 12 of the endoscope. In the present embodiment, the tubes 211 to 213 are bound by the string 224a, 224b. In an embodiment illustrated in FIG. 37, a fixing member 226 comprises a base portion 226a secured to the operation section 12 and plural sets of clamping ribs 226b, 226c and 226d into which the tubes 211 to 213 are resiliently inserted.

FIG. 38 depicts still another embodiment of the fixing member. A fixing member 228 comprises a hook 228a and a rubber band 228b which is secured to the hook such that the tubes 211 to 213 are enclosed by the rubber band. In an embodiment shown in FIG. 39, a fixing member 230 is constructed by a so-called SK band whose base portion 230a is secured to the outer surface of the operation section 12. In an embodiment illustrated in FIG. 40, a fixing member 232 comprises a sucker portion 232a secured to the operation section 12 and a ring portion 232b having a flat bottom surface which is sucked to the sucker. FIG. 41 depicts still another embodiment of the fixing member. In this embodiment, a fixing member 234 comprises an adhesive tape 234a secured to the operation section 12, an adhesive layer 234b applied on an outer surface of the tape and a cover sheet 234c applied on the adhesive layer. A flat bottom wall of a multilumen tube 235 is secured to the adhesive layer 234b. It should be noted that the fixing members of the previous embodiments may be equally used to fix the multilumen tube.

In the embodiment shown in FIG. 32, the conduit tubes 201 are fixed to the operation section 12, universal cord 21 and connector 202 by means of the fixing members 203, 204 and 205. However, according to the invention, it is not always necessary to secure the conduit tubes to all of these construction members, but may be secured to at least one of these construction members. Further it is not necessary to form the fixing members 203 to 205 in the same construction, but may be formed to have suitable construction. Moreover, the fixing member 203 may be secured to the mold type operation section cover 171 as shown in FIG. 42.

Now several embodiments of the operation section cover according to the invention will be explained. In these embodiments, the operation section cover is formed as a sheet for wrapping the operation section of the endoscope.

In FIG. 43, an operation section cover 240 is shown as an exploded condition. When the operation section 12 of the endoscope is covered with the operation section cover 240, the cover is folded as shown by arrows to wrap the operation section. In this case, it is difficult to find the edge of the cover 240 upon removing the cover from the operation section. The following embodiments can mitigate such a disadvantage. That is to say, in these embodiments, there is provided means for indicating the edge of the operation section cover. This indicating means may be preferably formed as color, marks, protrusions or depressions. In FIG. 44, a sheet-like operation section cover 242 comprises colored edges 242a. In this case, the whole edge may be colored with same color, but in the present embodiment, edge portions denoted by U, V and W are colored with different colors. Then the edge of the cover 242 can be found much more easily.

In FIG. 45, an operation section cover 244 comprises a ridge 244a along its outer edge. Instead of the ridge 244a, a depression may be formed along the edge of the operation section cover. FIG. 46 illustrates another embodiment of the operation section cover according to the invention. In the present embodiment, an operation section cover 246 comprises marks 246a, 246b and 246c recorded along the edge of the cover. The marks 246a to 246c are different from each other, but they may be identical with each other.

FIG. 47 is a perspective view showing an embodiment of a hanger for supporting the endoscope for use in the endoscope system according to the invention. A hanger 256 comprises a supporting stud 257, universal cord side supporting member 258, angle knob shaft supporting member 259 and fixing member 260. The universal cord side supporting member 258 and angle knob shaft supporting member 259 are secured to each other and the supporting member 258 is slidable along the supporting stud 257 and may be set at any desired level by means of the fixing member 260. In the supporting member 258 there is formed a recess 258a into which the universal cord 21 may be inserted. In the present embodiment, an operation section cover 261 is constructed similarly to the operation section cover 171 shown in FIG. 30. That is to say, the mold type operation section cover 261 comprises main body halves which are coupled with each other along a boundary surface 262 and the shafts 263 protrude from one of the main body halves and the angle knobs 33 may be detachably secured to the shafts 263. A distance D1 between the boundary surface 262 and an rear surface of the angle knobs 33 is made smaller than a distance D2 between the center of the recess 258a formed in the universal cord side supporting member 258 and an outer surface of the angle knob shaft supporting member 259. Then, after the examination, when the assembly of the endoscope and the disposable protection cover is set on the hanger 256, the angle knobs 33 are automatically removed from the shafts 263 as shown in FIG. 47. Therefore, it is no longer necessary to manually remove the angle knobs 33 from the shafts 263, and thus the operation for removing the protection cover can be simplified and shortened.

In the embodiment shown in FIGS. 5 to 9, the endoscope is of a direct viewing type in which a viewing optical axis is parallel with a longitudinal axis of the insertion section and the insertion section cover is constructed to allow such direct view. That is to say, the assembly of the insertion section of the endoscope and insertion section cover can effect the direct view. According to the present invention, the insertion section cover may be formed to allow side viewing even if the endoscope is of the direct view type.

Figure 48:
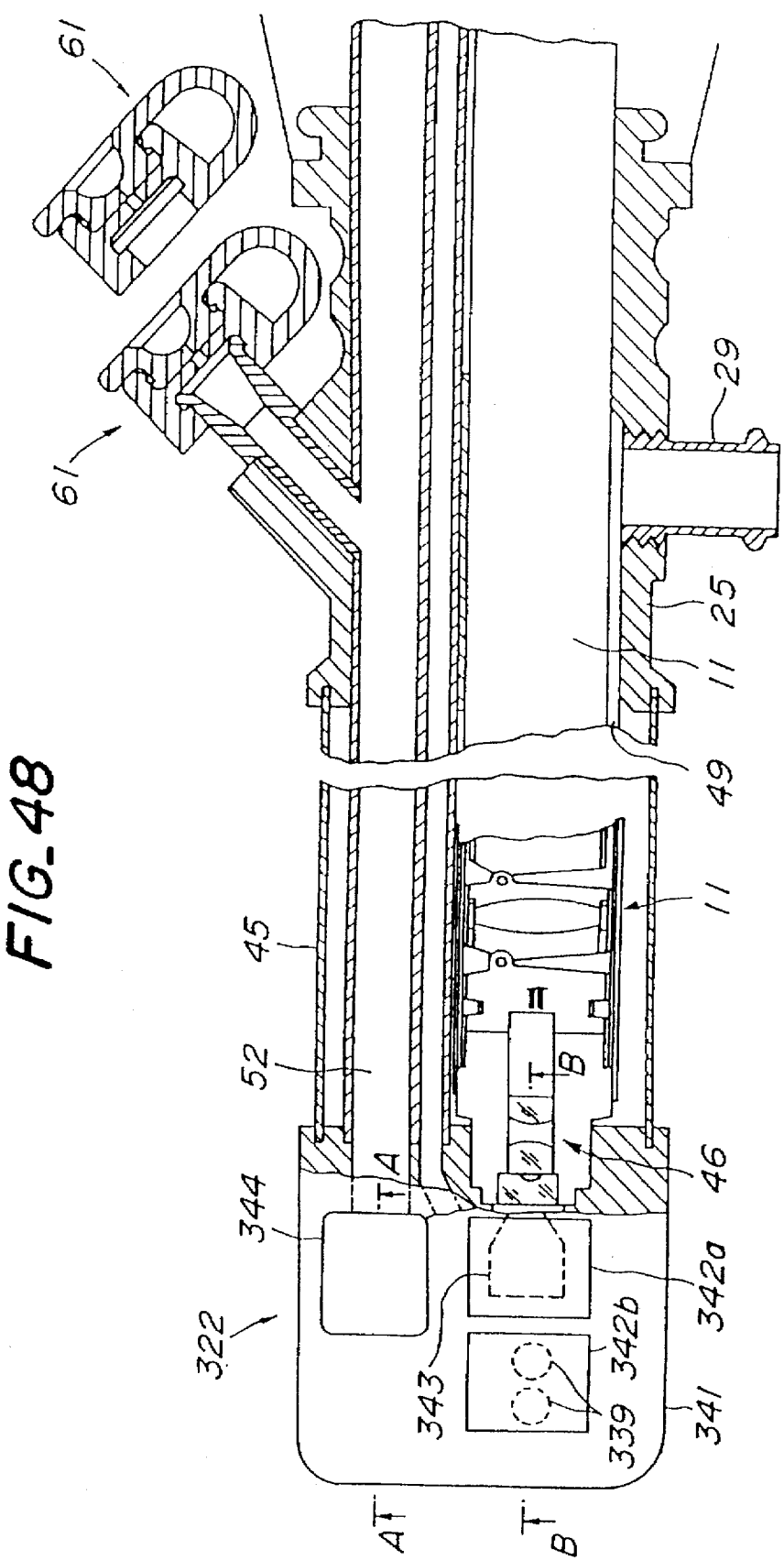
FIG. 48 is a cross sectional view illustrating another embodiment of the insertion section cover according to the invention.

FIG. 48 shows an embodiment of the side viewing type insertion section cover of the endoscope system according to the invention, and FIGS. 49 and 50 are cross sectional views cut along lines A—A and B—B, respectively in FIG. 48. A distal end construction member 341 of an insertion section cover 322 comprises a forceps outlet 344 which is opened in a side wall of the distal end construction member as shown in FIG. 49, an observation window 342a, and an illumination window 342b. These windows 342a and 342b are also provided on the side wall of the distal end construction member 341. The distal end construction member 341 further comprises a prism 343 arranged on a rear surface of the observation window 342a and a pair of light guide optical elements 339 for guiding the illumination light transmitted by the light guide optical fiber bundles 39 to the illumination window 342b as depicted in FIG. 50. It should be noted that the prism 343 and light guide optical elements 339 are arranged such that the illumination light is transmitted through the light guide optical elements 339 and exits from the illumination window 342b to illuminate the cavity wall and light reflected from the cavity wall is made incident upon the observation window 342a, reflected by the prism 343 and is then made incident upon the objective lens system 46 of the endoscope. In this manner, the assembly of the insertion section of the direct viewing type endoscope and the insertion section cover 322 can be used as a side viewing type endoscope.

Figure 51:
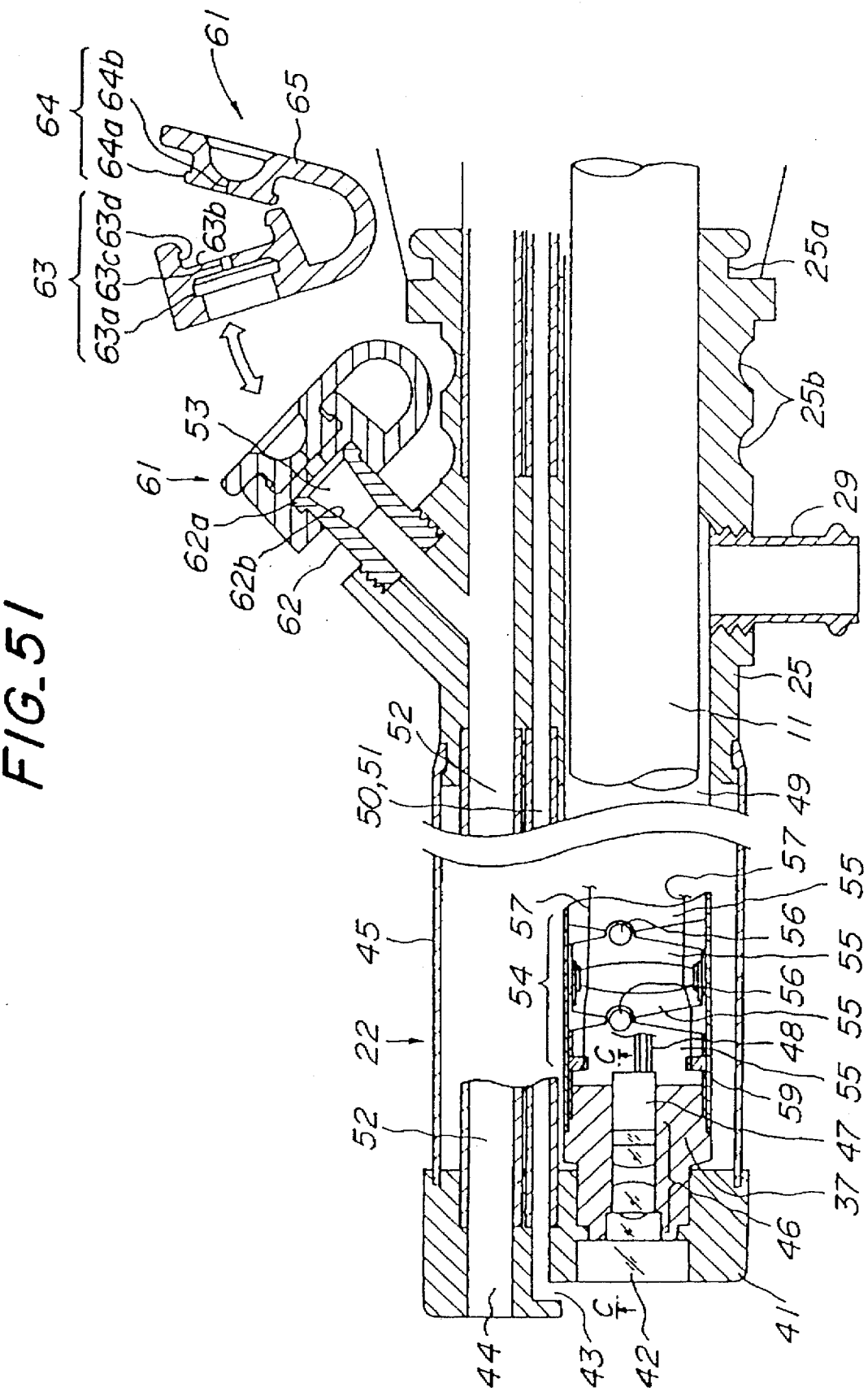
FIG. 51 is a cross sectional view showing another embodiment of the insertion section cover according to the invention.

FIG. 51 shows the insertion section cover 22 of the direct viewing type and FIG. 52 is a cross sectional view cut along a line C—C in FIG. 51. It should be noted that the insertion section inserting channel 49 of the direct viewing type insertion section cover 22 is formed to have the same shape and size as those of the side viewing type insertion section cover 322 shown in FIG. 48. Therefore, by inserting the insertion section 11 of the direct viewing type endoscope into the direct viewing type insertion section cover 22 or the side viewing type insertion section cover 322, the assembly can be used as a direct viewing type endoscope or a side viewing type endoscope. In other words, it is no longer necessary to provide a side viewing type endoscope.

FIG. 53 is shows another embodiment of the side viewing type insertion section cover according to the invention. In the embodiment illustrated in FIGS. 48 to 50, the prism 343 is used to bend the observation optical axis, if in the present embodiment a reflection mirror 345 is arranged within the distal end construction member 341. The remaining construction is the same as the previous embodiment.

In the case of using the mirror 345 for converting a direct viewing optical system into a side viewing optical system, the image is reversed in an up-side-down manner. This is inconvenient for the actual examination. According to the invention, this inconvenience can be removed by suitably constructing the video processor for processing the image signal generated by the CCD image sensor.

FIG. 54 is a block diagram showing an embodiment of the video processor for processing the image signal generated by a CCD 380. The video processor comprises pre-processor 381, A/D converter 382, memory 383, D/A converter 384 and a host-processor 385. The image signal processed by the host-processor 385 is supplied to a monitor 386. In the present embodiment, the memory 383 is constructed such that it can assume one of two operation modes, i.e. a normal mode in which successive lines of the image signal are stored in a normal order and are read out also in a normal order, and a reverse mode in which successive lines of the image signal are stored in a reverse order of normal order and are read out in a normal order to reverse mode. Therefore, when the side viewing type insertion section cover is used, the memory 383 is driven in the reverse mode and the image is reversed in an up-side-down manner. When the direct viewing insertion section cover is used, the memory 383 is driven in the normal mode. In this manner, the reversed image obtained by using the side viewing type insertion section cover can be corrected. According to the invention, the reversal of the image can be corrected by using a CCD with a reverse read-out faculty.

In the case of effecting the above mentioned reversed image correction, it is desired that the operator can clearly know the reversal of the image. This can be realized by a displaying means. In an embodiment shown in FIG. 55, an indicator lamp 391 is provided on the video processor 15, and when the reverse mode is selected, the lamp is lit on. It should be noted that the indicator lamp 391 may be periodically turned on and off or the lamp 391 is usually lit and only in the reverse mode, it may be turned off or on and off. In an embodiment illustrated in FIG. 56, a reverse mark 392 is displayed on the monitor 16 when the reverse mode is selected. Alternatively the selection of the reverse mode may be represented by sound instead of the above mentioned visual alarm or in addition to the visual alarm.

What is claimed is:

1. An endoscope system comprising:

an endoscope having an insertion section for inserting into a cavity under inspection and an operation section to which a proximal end of the insertion section is connected; and a protection cover having an insertion section cover for covering said insertion section of the endoscope and conduit channels extending within said insertion section cover, wherein said endoscope comprises a bending portion which has a first radius of curvature of bending movement in a first direction, which is opposite to a second direction in which said conduit channels are arranged viewed in a radial direction of said endoscope, said first radius of curvature being smaller than a second radius of curvature of bending movement of the bending portion in said second direction, wherein when the insertion section and the insertion section cover are assembled together, the resultant assembly has a radius of curvature in said first direction which is substantially equal to the radius of curvature of the resultant assembly in said second direction.

2. An endoscope system according to claim 1, wherein said first and second radii of curvature of bending movement in the first and second directions are set such that an assembly of the insertion section cover of the protection cover and the insertion section of the endoscope is bent substantially symmetrically in the first and second direction.

3. A protection cover for use in an endoscope system including an endoscope having an insertion section for insertion into a cavity under inspection and an operation section to which a proximal end of the insertion section is connected, said insertion section having a semicircular cross-sectional configuration, said protection cover comprising:

an insertion section cover for covering said insertion section of the endoscope;

a multilumen tube having a non-circular cross-sectional configuration at first and second ends of said mutilumen tube and disposed within said insertion section cover to extend from a proximal end to a distal end of said insertion section cover, a plurality of conduit channels being formed in said multilumen tube and extending from said proximal end to said distal end, said cross-sectional configuration of said multilumen tube at said first end having a size which is substantially identical to a size of said cross-sectional configuration of said multilumen tube at said second end.

4. A protection cover according to claim 3, wherein said cross-sectional configuration of said multilumen tube is substantially semicircular.

5. A protection cover according to claim 3, wherein said cross-sectional configuration of said multilumen tube is substantially elliptical.

6. A protection cover system for use in an endoscope system including an endoscope having an insertion section for insertion into a cavity under inspection and an operation section to which a proximal end of the insertion section is connected, said protection cover system comprising:

a plurality of individual protection covers, each having a forceps channel and insertion section cover having an insertion section channel, wherein each of said protection covers has at least one of (i) a diameter of the forceps channel, (ii) a length of the insertion section cover, and (iii) a diameter of said insertion section channel which is different from a corresponding one of each of the other protection covers and each of said protection covers further has (i) a first recess formed therein for connecting said insertion section cover with an operation section cover, (ii) a second recess formed therein for aiding in supporting the protection cover, and (iii) a nipple for use in inflating the cover, and one of said first recess, said second recess and said nipple is commonly formed for all of said protection covers.

\* \* \* \* \*